United States Patent
Carmi et al.

(10) Patent No.: US 12,295,777 B2
(45) Date of Patent: May 13, 2025

(54) METHOD AND WORKSTATION FOR GENERATING A JOINT-VISUALIZATION IMAGE BASED ON MULTIPLE FUNCTIONAL IMAGING DATASETS

(71) Applicant: GE Precision Healthcare LLC, Wauwatosa, WI (US)

(72) Inventors: Raz Carmi, Haifa (IL); Jonathan Sachs, Haifa (IL)

(73) Assignee: GE Precision Healthcare LLC, Wauwatosa, WI (US)

( * ) Notice: Subject to any disclaimer, the term of this patent is extended or adjusted under 35 U.S.C. 154(b) by 483 days.

(21) Appl. No.: 17/720,584

(22) Filed: Apr. 14, 2022

(65) Prior Publication Data

US 2023/0329660 A1 Oct. 19, 2023

(51) Int. Cl.
*A61B 6/00* (2024.01)
*A61B 6/46* (2024.01)
*G06T 3/14* (2024.01)
*G06T 5/50* (2006.01)

(52) U.S. Cl.
CPC ............ *A61B 6/5235* (2013.01); *A61B 6/461* (2013.01); *G06T 3/14* (2024.01); *G06T 5/50* (2013.01); *G06T 2207/10072* (2013.01); *G06T 2207/20221* (2013.01)

(58) Field of Classification Search
None
See application file for complete search history.

(56) References Cited

U.S. PATENT DOCUMENTS

| | | | |
|---|---|---|---|
| 8,525,852 B2 | 9/2013 | Dresel | |
| 9,220,438 B2 | 12/2015 | Kaftan | |
| 9,788,725 B2 | 10/2017 | Xiao | |
| 11,030,748 B2 * | 6/2021 | Carmi | A61B 6/032 |
| 11,557,069 B2 * | 1/2023 | Senzig | G16H 50/30 |
| 2019/0332900 A1 * | 10/2019 | Sjolund | G06T 9/002 |

FOREIGN PATENT DOCUMENTS

WO WO-2019149529 A1 * 8/2019 ............ A61B 6/037

OTHER PUBLICATIONS

68Ga- and 177Lu-Labeled PSMA I&T: Optimization of a PSMA-Targeted Theranostic Concept and First Proof-of-Concept Human Studies, by Weineisen et al., J Nucl Med 2015; 56:1169-1176; DOI: 10.2967/jnumed.115.158550 (Year: 2015).*

* cited by examiner

*Primary Examiner* — Vikkram Bali

(57) ABSTRACT

A method and workstation for combining multiple functional imaging datasets into a joint-visualization image. In one aspect, a method of functional imaging includes accessing a plurality of functional imaging datasets acquired from a volume-of-interest, wherein each of the plurality of functional imaging datasets is a different one of a plurality of functional imaging data types. The method includes registering the plurality of functional imaging datasets and determining a visualization priority for each of a plurality of pixels in a joint-visualization image based on a logical comparison of corresponding information in each of the plurality of functional imaging datasets. The method includes generating the joint-visualization image based on the visualization priority and at least a portion of each of the plurality of functional imaging datasets, wherein each of a plurality of pixels in the joint-visualization image represents only a single one of the plurality of functional imaging data types.

18 Claims, 16 Drawing Sheets

METHOD AND WORKSTATION FOR GENERATING A JOINT-VISUALIZATION IMAGE BASED ON MULTIPLE FUNCTIONAL IMAGING DATASETS

BACKGROUND

Functional imaging is a field of diagnostic imaging that focuses on detecting and/or measuring changes in a patient related to blood flow or the absorption of particular molecules. Molecular imaging, such as Single-photon emission computed tomography (SPECT) and Positron emission tomography (PET), and Functional magnetic resonance imaging (fMRI), are non-limiting examples of functional imaging modalities.

In medical molecular imaging, an administered radiotracer is typically based on a ligand molecular or chemical component with an attached radioactive isotope. The ligand is usually designed to mark, or be attached to, specific physiological components or processes in the patient body, and the radioactive isotope emits a gamma-photon, or alternatively a positron, which in turn results in the emission of two gamma rays. The ligand molecule can be attached to a selected specific protein. For example, certain proteins that are overexpressed in tumors and metastasizes. The ligand may be based on molecules that are entered into cells as part of a specific physiological process such as glucose metabolism. The ligand part of the tracer may be selected to flow in the blood circulation to enable the imaging of the vascular system. The radioactive isotope may be chemically connected to the ligand molecule, or it can replace one or more of the atoms in the natural ligand molecule to generate synthetic modified molecule (e.g., in $^{18}$F-FDG the Flourine-18 isotope replaces an oxygen-based atom group within a natural glucose molecule). In some radiotracers, the radioactive isotope can also serve as the ligand itself, such as in radioactive Iodine (e.g., $^{123}$I) which is strongly absorbed by thyroid cells. Another example is the $^{82}$Rb isotope which is used for Cardiac PET imaging since it has activity very similar to that of a potassium ion and it is rapidly extracted by the myocardium proportional to blood flow. In these tracers, the $^{123}$I or $^{82}$Rb are administered as a salt-like molecule with sodium or chlorine atoms respectively. In addition, there are materials which are used at the same time for radiotherapy and for imaging such as $^{177}$Lu-PSMA.

Positron emission tomography (PET) is a functional imaging technique that involves administering a radiotracer (also known as a radionuclide or a radiopharmaceutical) to a patient and then generating images to visualize the distribution and concentration of the radiotracer within the patient. Positron emission tomography (PET) is oftentimes used to help visualize biochemical changes within the patient's body, such as the patient's metabolism. Each PET radiotracer includes an organic ligand. Each PET radiotracer is configured to emit positrons. Positron emission tomography (PET) images the distribution of the radiotracer based on the positrons emitted from the positron-emitting isotope. The positrons interact with electrons in the patient's body, releasing gamma rays which are detected by the detectors of the PET imaging system.

One of the most common PET radiotracers is fluorodeoxyglucose ($^{18}$F-FDG) that includes a fluorine-18 ($^{18}$F) as the positron-emitting isotope. However, there are any other PET radiotracers in addition to $^{18}$F-FDG that may include one or both of a different positron-emitting isotope or a different ligand. Two examples of other PET radiotracers include $^{68}$Ga-PSMA-11 and $^{68}$Ga-DOTATOC. Both $^{68}$Ga-PSMA-11 and $^{68}$Ga-DOTATOC use gallium-68 ($^{68}$Ga) as the positron-emitting isotope instead of fluorine-18 ($^{18}$F). Additionally, the $^{68}$Ga is bound to a different ligand in both $^{68}$Ga-PSMA-11 and $^{68}$Ga-DOTATOC compared to $^{18}$F-FDG. Some radiotracers may be more specific or sensitive than others to specific diseases, organs, physiological situations, or medical conditions. As such, using more than one type of radiotracer may prove advantageous when imaging and diagnosing a patient due to the different sensitivities of the various radiotracers.

Single photon emission computed tomography (SPECT) is a functional imaging technique that involves administering a radiotracer to the patient and then detecting radiation emitted from the radiotracer in order to generate an image. Examples of radiotracers commonly used in SPECT imaging include Iodine-123 ($^{123}$I), $^{99m}$Tc-MDP, and $^{99m}$Tc-MIBI. As with PET imaging, the various different radiotracers used for SPECT imaging may each be more specific or sensitive to certain diseases, organs, physiological situations, or medical conditions. It may, therefore, be advantageous to utilize more than one SPECT radiotracer in order to improve the diagnosis of a patient.

Functional magnetic resonance imaging (fMRI) is another type of functional imaging that may be used to obtain functional images of a patient. Instead of relying on a radiotracer, like both PET and SPECT, fMRI instead images the patient using a strong magnetic field and radio-frequency energy. An fMRI image may be more specific or sensitive to specific diseases, organ, physiological situations or medical conditions than either PET imaging or SPECT imaging. Due to the various sensitivities, etc. of the various types of functional images, it may be desirable to visualize information representing various different functional imaging data types into a single image. Conventional techniques have attempted to visualize multiple different functional imaging data types at the same time in a single image. For example, conventional techniques have registered images representing different types of functional imaging data into a single fused image. In some conventional approaches, a first type of functional imaging data will be represented in a first color and a second type of functional imaging data will be represented in a second color. In some conventional approaches, a first functional image (represented in a first color) is overlaid with a second functional image (represented in a second color) and displayed in a single fused image. However, it is typically very difficult to achieve satisfactory visual clearness by simply overlaying or blending the first functional image with the second functional image. Adding multiple layers of information, that are displayed at the same time, may create visual confusion for the user and may result in the generation or creation of undesired hues/colors when the first functional image and the second functional image are combined/blended into the fusion image.

For these and other reasons there is a need for an improved method and workstation for functional imaging in order to generate and display a joint-visualization image representing a plurality of functional imaging datasets.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method of functional imaging includes accessing a plurality of functional imaging datasets acquired from a volume-of-interest, wherein each of the plurality of functional imaging datasets is a different one of a plurality of functional imaging data types. The method includes registering the plurality of functional imaging datasets to each other. The method includes determining a visualization priority for each of a plurality of pixels in a joint-visualization image based on logical comparison of corresponding information in each of the plurality of functional imaging datasets, wherein the visualization priority defines which one of the plurality of functional imaging data types will be represented by each of the plurality of pixels. The method includes generating the joint-visualization image based on the visualization priority determined for each of the plurality of pixels and at least a portion of each of the plurality of functional imaging datasets, wherein the joint-visualization image represents information from each of the plurality of functional imaging data types at the same time, and wherein each of the plurality of pixels in the joint-visualization image represents only a single one of the plurality of functional imaging data types. The method includes displaying the joint-visualization image on a display device.

In another embodiment, a workstation includes a display device and a processor. The processor is configured to access a plurality of functional imaging datasets acquired from a volume-of-interest, wherein each of the plurality of functional imaging datasets is a different one of a plurality of functional imaging data types. The processor is configured to register the plurality of functional imaging datasets to each other. The processor is configured to determine a visualization priority for each of a plurality of pixels in a joint-visualization image based on a logical comparison of corresponding information in each of the plurality of functional imaging datasets, wherein the visualization priority defines which one of the plurality of functional imaging data types will be represented by each of the plurality of pixels. The processor is configured to generate the joint-visualization image based on the visualization priority determined for each of the plurality of pixels and at least a portion of each of the plurality of functional imaging datasets, wherein the joint-visualization image represents information from each of the plurality of functional imaging data types at the same time, and wherein each of the plurality of pixels in the joint-visualization image represents only a single one of the plurality of functional imaging data types. The processor is configured to display the joint-visualization image on the display device.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
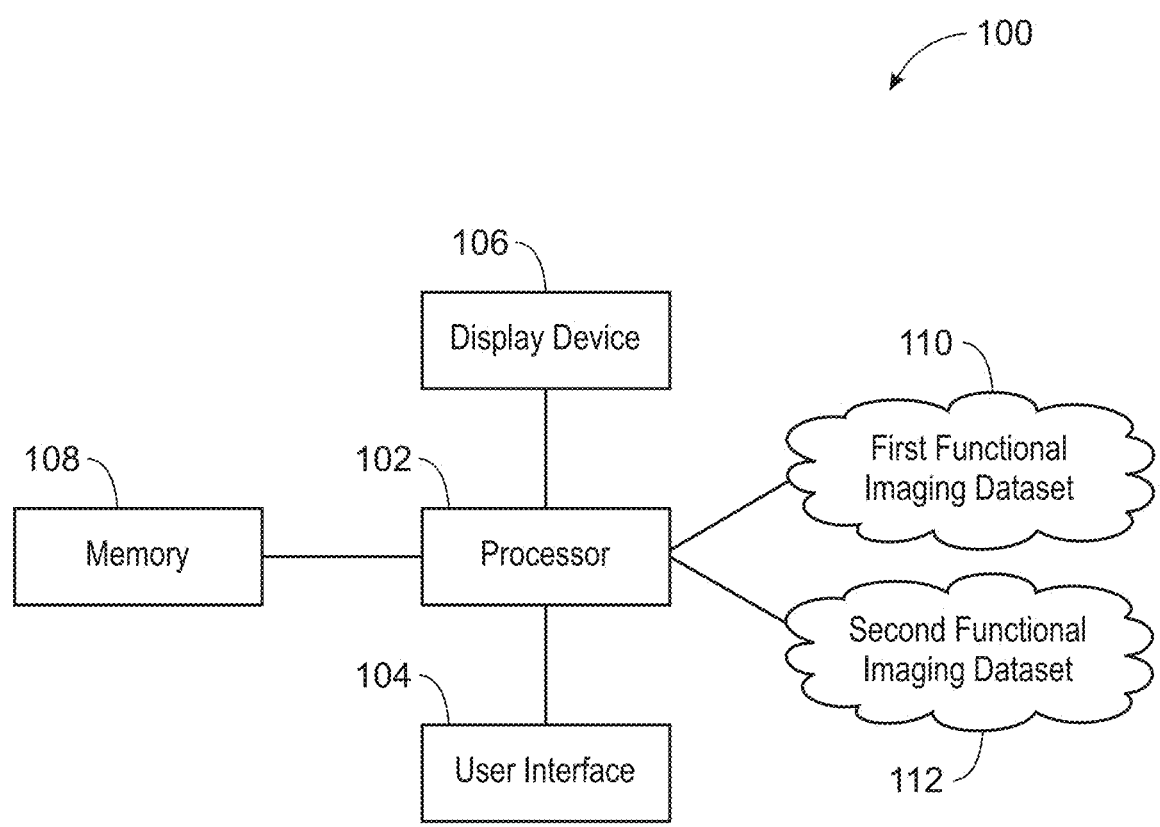
FIG. 1 is a schematic representation of a workstation in accordance with an embodiment.

FIG. 1 depicts a workstation 100 in accordance with an embodiment. The workstation 100 shown in FIG. 1 includes a processor 102, a user interface 104, a display device 106, and a memory 108. The memory 108 may be random access memory (RAM) according to an embodiment. The processor 102 may include a CPU according to an embodiment. According to other embodiments, the processor 102 may include other electronic components capable of carrying out processing functions, such as a GPU, a microprocessor, a DSP, a field-programmable gate array (FPGA), or any other type of processor capable of performing logical operations. According to other embodiments, the processor 102 may include multiple electronic components capable of carrying out processing functions. For example, the processor 102 may include two or more electronic components selected from a list of electronic components including: a CPU, a DSP, an FPGA, and a GPU.

The user interface 104 may be used to control operation of the workstation 100. The user interface 104 may be used to control the input of patient data, or to select various modes, operations, parameters, and the like. The user interface 104 may include one or more user input devices such as a keyboard, hard keys, a touch pad, a track ball, rotary controls, sliders, soft keys, or any other user input devices. According to some embodiments, the user interface 104 may include a touch panel that is part of a touchscreen. An exemplary touchscreen will be described hereinafter with respect to FIG. 2.

The workstation 100 includes a display device 106. The display device 106 may include any type of display screen or display that is configured to display images, text, graphical user interface elements, etc. The display device 106 may be, for example, a cathode ray tube (CRT) display, a light-emitting diode (LED) display, an organic light-emitting diode (OLED) display, a liquid crystal display (LCD), etc. According to some embodiments, the display device 106 may be a display screen that is a component of a touchscreen.

Figure 2:
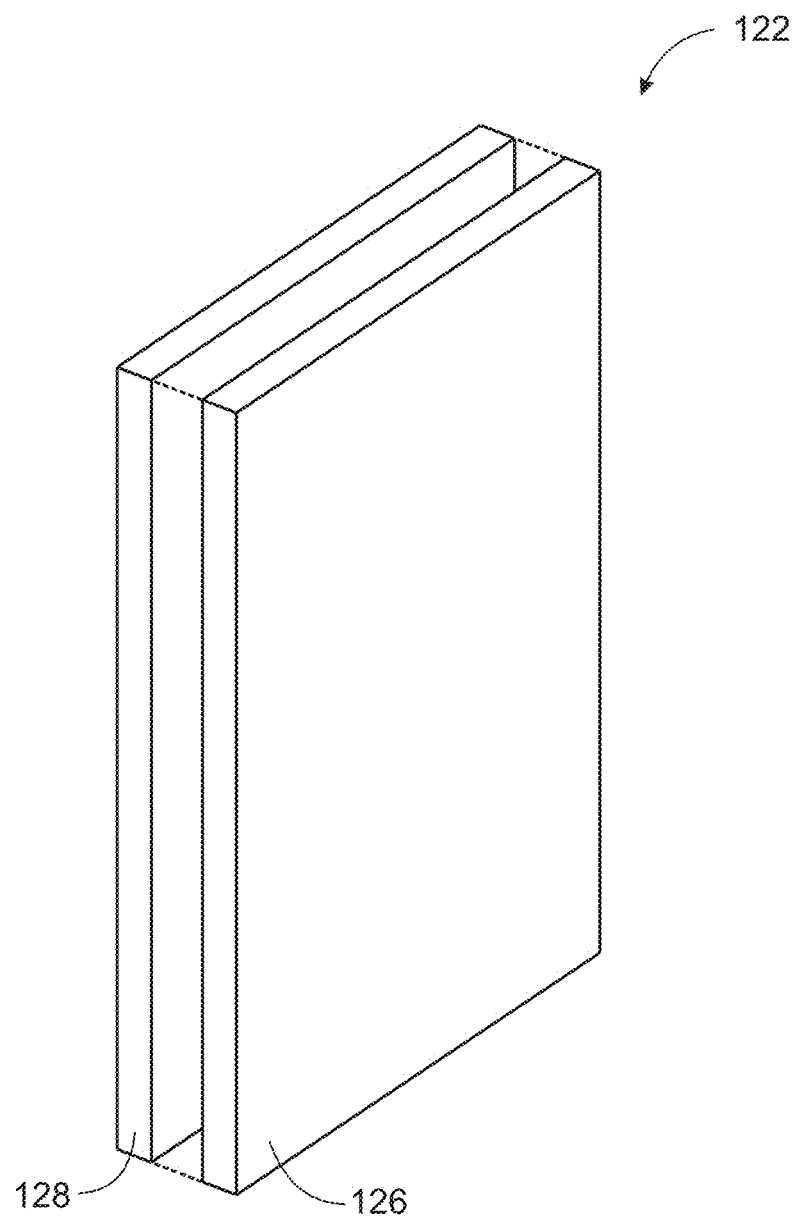
FIG. 2 is an exploded representation of a touchscreen in accordance with an embodiment.

As discussed above, the display device 106 and the user interface 104 may be components in a touchscreen. FIG. 2 is an exploded representation of a touchscreen 122 in accordance with an exemplary embodiment. The touchscreen 122 includes a touch panel 126 and a display screen 128 in accordance with an embodiment. The touch panel 126 may be located behind the display screen 128 or in front of the display screen 128 according to various non-limiting examples. For embodiments where the touch panel 126 is positioned in front of the display screen 128, the touch panel 126 may be configured to be substantially transparent so that the user may see images displayed on the display screen 128. The touch panel 126 may utilize any type of technology configured to detect a touch or gesture applied to the touch panel 126 of the touchscreen 122. As discussed hereinabove, the display device 118 may include a display screen of a touchscreen such as the display screen 128, and the user interface 115 may include a touch panel, such as the touch panel 126 of the touchscreen 122. The touch panel 126 may be configured to detect single-point touch inputs and/or multi-point touch inputs according to various embodiments. The touch panel 126 may utilize any type of technology configured to detect a touch or gesture applied to the touch panel 126 of the touchscreen 122. For instance, the touch panel 126 may include resistive sensors, capacitive sensors, infrared sensors, surface acoustic wave sensors, electromagnetic sensors, near-field imaging sensors, or the like. Some embodiments may utilize the touch panel 126 of the touchscreen 122 to provide all of the user interface functionalities for the workstation 100, while other embodiments may also utilize one or more other components as part of the user interface 104. The processor 102 may be configured to access one or more functional imaging datasets.

Figure 3:
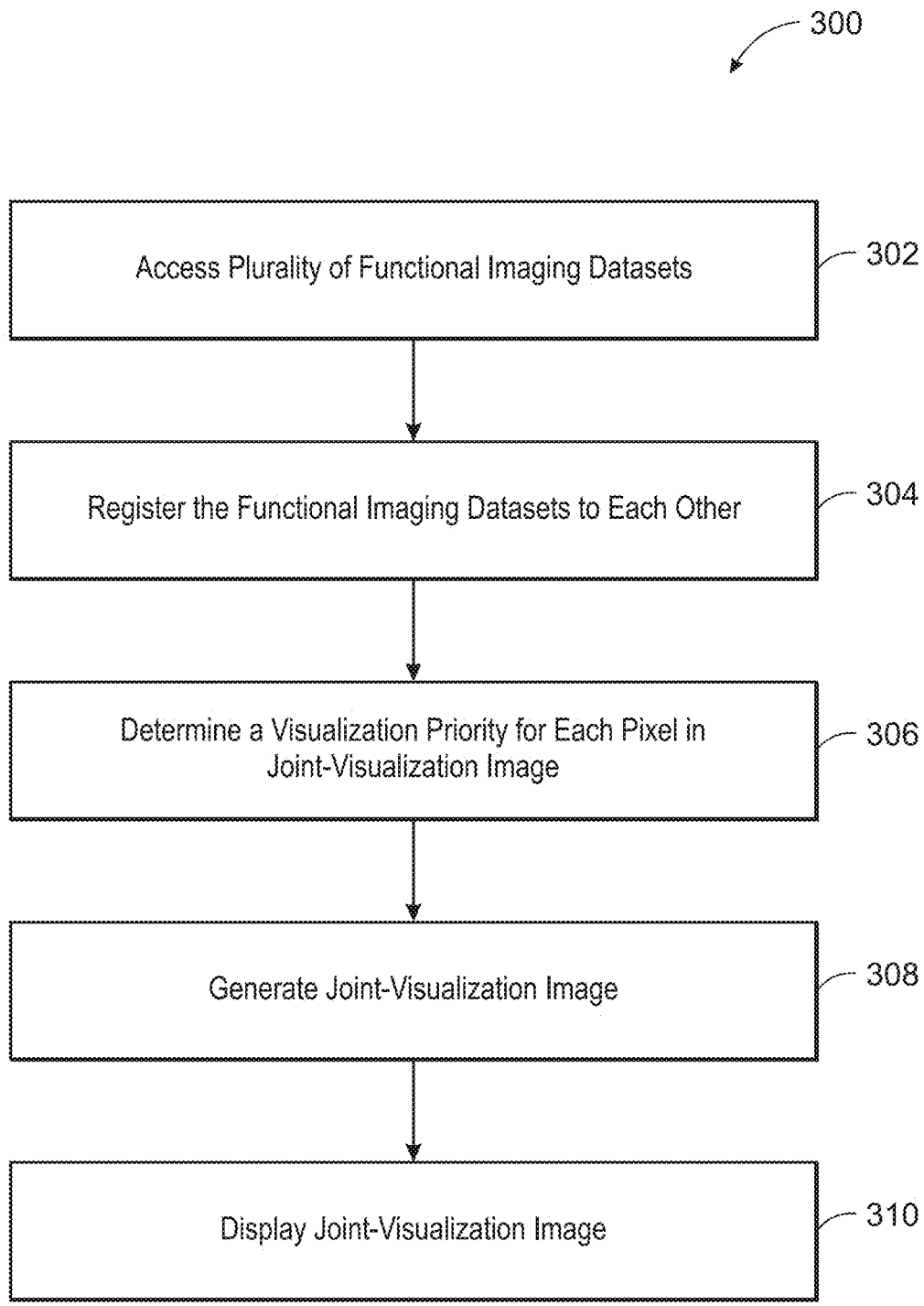
FIG. 3 is a flowchart of a method in accordance with an embodiment.

FIG. 3 illustrates a flowchart of an embodiment of a method 300. The method 300 shown in FIG. 3 may be performed with a workstation, such as the workstation 100 shown in FIG. 1. The technical effect of the method 300 is the display of joint-visualization image on the display device 106. The joint-visualization image represents information from a plurality of functional imaging data types at the same time. FIG. 3 will be described according to an exemplary embodiment using the workstation 100 shown in FIG. 1.

At step 302, the processor 102 accesses a plurality of functional imaging datasets acquired from a volume-of-interest. The workstation may, for instance, access the plurality of functional imaging datasets from a memory or storage, from a Picture archiving and communication system (PACS), from a local server, from a remote server, or directly from one or more imaging systems. Each of the plurality of functional imaging datasets is a different one of a plurality of functional imaging data types. A first functional imaging dataset 110 and a second functional imaging dataset 112 are schematically represented with respect to the workstation 100. According to an exemplary embodiment, the processor 102 may be configured to access the first functional imaging dataset 110 and the second functional imaging dataset 112. According to other embodiments, the processor 102 may be configured to access more than two different functional imaging datasets. The data in one or more of the functional datasets may include quantitative values, which may be in either physical units or calibrated according to a standard calibrated scale, or one or more of the functional imaging datasets may include values in an arbitrary scale. The arbitrary scale may, for instance, be determined based on the image acquisition parameters and/or the amount of radiopharmaceutical administered to the patient. Additional information about the functional imaging datasets will be discussed hereinbelow.

Each of the plurality of functional imaging datasets is a different functional imaging data type. The functional imaging data type may refer to one or both of a functional imaging modality used to acquire each respective functional imaging dataset or the radiotracer used to acquire each respective functional imaging dataset. Positron emission tomography (PET) imaging, single photon computed emission tomography (SPECT) imaging, and functional magnetic resonance imaging (fMRI) are non-limiting examples of different functional imaging modalities. A positron emission tomography (PET) dataset is acquired with a positron emission tomography (PET) imaging system; a single photon computed emission tomography (SPECT) dataset is acquired with a single photon computed emission tomography (SPECT) imaging system; and a functional magnetic resonance imaging (fMRI) dataset is acquired with a functional magnetic resonance imaging (fMRI) imaging system. For purposes of this disclosure, a first functional imaging dataset acquired with a different functional imaging modality than a second functional imaging dataset is considered to be a different functional imaging data type than the second functional imaging dataset. For example, a first functional imaging dataset acquired with a Positron emission tomography (PET) imaging system is a different functional imaging data type than a second functional imaging dataset acquired with either a positron emission tomography (PET) imaging system using a different radiotracer, a single photon computed emission tomography (SPECT) imaging system or a functional magnetic resonance imaging (fMRI) imaging system.

According to various embodiments, one or more of the plurality of functional imaging datasets acquired at step 302 may have been acquired with a hybrid, or multi-modality imaging system. Examples of hybrid, or multi-modality, imaging systems include, but are not limited to a PET-CT imaging system, a SPECT-CT imaging system, a PET-MRI imaging system, a SPECT-MRI imaging system, and an MRI-CT imaging system. According to various embodiments, the hybrid imaging systems involving an MRI imaging system, such as the PET-MRI imaging system, the SPECT-MRI imaging system, and the MRI-CT imaging system may use an fMRI imaging system configured to obtain MRI data that is functional imaging data.

Figure 4:
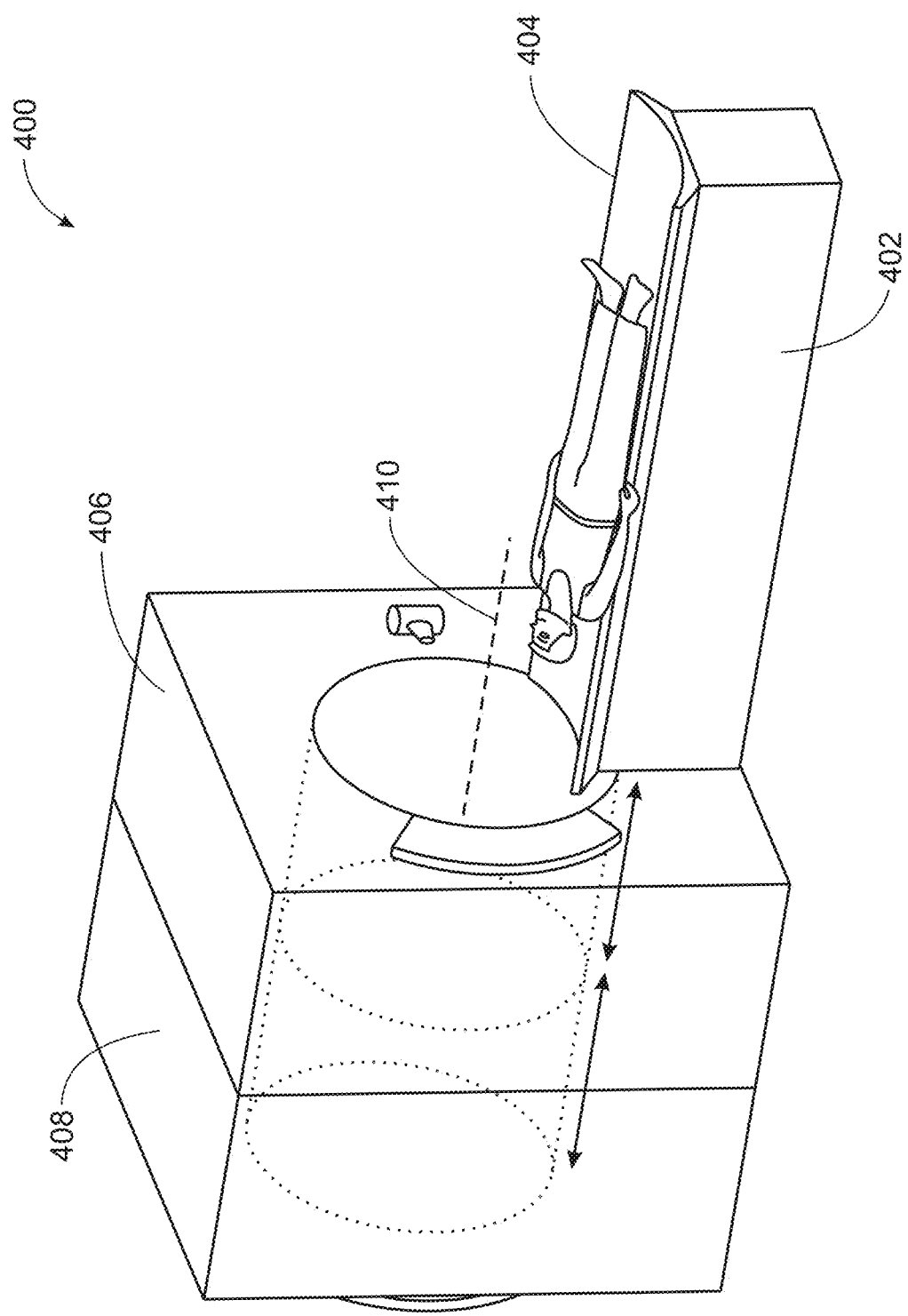
FIG. 4 is a schematic representation of a hybrid imaging system in accordance with an embodiment.

FIG. 4 is a schematic representation of a hybrid imaging system 400. The hybrid imaging system 400 includes a patient support 402 supporting a bed 404. The hybrid imaging system 400 includes a first imaging system 406 and a second imaging system 408. According to an exemplary embodiment, the first imaging system 406 and the second imaging system 408 may share a common bore. A bore centerline 410 is shown in FIG. 4. The patient bed 404 is configured to be translated into the bore of the hybrid imaging system 400.

The first imaging system 406 may be a first type of imaging system, such as an MRI imaging system, a CT imaging system, a SPECT imaging system, or a PET imaging system. The second imaging system 408 may be a different type of imaging system. The second imaging system 408 may, for instance, be an MRI imaging system, a CT imaging system, a SPECT imaging system, or a PET imaging system. According to an embodiment, the first imaging system 406 may be a functional imaging system, such as a SPECT imaging system, a PET imaging system, or a fMRI imaging system. And the second imaging system 408 may be an anatomical imaging system, such as a CT imaging system or an MRI imaging system.

According to various embodiments, the relative positioning of the anatomical imaging system and the functional imaging system may be switched. For example, the first imaging system may be an anatomical imaging system, such as a CT imaging system or an MRI imaging system. And, the second imaging system may be a functional imaging system, such as a SPECT imaging system, a PET imaging system, or a fMRI imaging system.

Each of the plurality of functional imaging datasets accessed at step 302 may have been acquired with a different type of imaging system, and each functional imaging dataset may represent a different functional imaging data type. For example, if a first of the plurality of functional imaging datasets was acquired with a SPECT imaging system, a second of the functional imaging datasets may have been acquired with a different type of functional imaging system, such as a PET imaging system or an fMRI imaging system. It should be appreciated by those skilled in the art that other embodiments may use functional imaging datasets that were acquired with imaging systems other than a PET imaging system, a SPECT imaging system, and an fMRI imaging system.

According to various embodiments, two or more of the functional imaging datasets may have been acquired with the same type of functional imaging system. For example, two or more of the functional imaging datasets may have been acquired with a PET imaging system, and/or two or more of the functional imaging datasets may have been acquired with a SPET imaging system. Both PET and SPECT imaging involves the use of a radiotracer. Most radiotracers includes a radioactive isotope bound to an organic ligand, which serves as a targeting agent. The ligand in each radiotracer is selected to interact with specific proteins. Clinicians may choose a radiotracer with a specific ligand in order to specifically target various proteins within the patient.

According to an embodiment where the plurality of functional imaging datasets were acquired with a PET imaging system, a first of the plurality of functional imaging datasets may have been acquired using a first radiotracer including a first ligand, and a second of the plurality of functional imaging datasets may have been acquired using a second radiotracer including a second ligand that is different than the first ligand.

According to an embodiment where the plurality of functional imaging datasets were acquired with a SPECT imaging system, a first of the plurality of functional imaging datasets may have been acquired using a first radiotracer including a first ligand, and a second of the plurality of functional imaging datasets may have been acquired using a second radiotracer including a second ligand that this different than the first ligand.

Next, at step 304, the processor 102 registers the plurality of functional imaging datasets to each other. According to embodiments where the functional datasets were acquired using a hybrid imaging system, such as the hybrid imaging system 400 shown in FIG. 4, each functional imaging dataset may already be registered to an anatomical dataset. For instance, each functional imaging dataset may be registered to a CT dataset. Registering a functional image dataset to an anatomical image dataset, when both datasets were acquired on the same hybrid imaging system, is generally a relatively easy task since the two datasets were acquired at times that were temporally close to each other and because the patient was in the same, or a very similar, position during the acquisition of both datasets. For most hybrid imaging systems, the functional imaging dataset may be registered to the anatomical imaging dataset using a rigid transformation, such as one or more linear translations and/or rotations. However, fully elastic image registration techniques may be used as well and are known in the art.

According to an embodiment, a first anatomical image dataset may be full-dose CT dataset, while a second anatomical image dataset may be a low-dose CT dataset. For example, the second anatomical image dataset may be acquired using a scout scan or other type of low-dose CT acquisition protocol to reduce the total dose received by the patient. Acquiring one or more low-dose CT datasets may be advantageous since the low-dose CT dataset works perfectly well for registration purposes and the first anatomical image dataset is a full-dose CT dataset.

Figure 5:
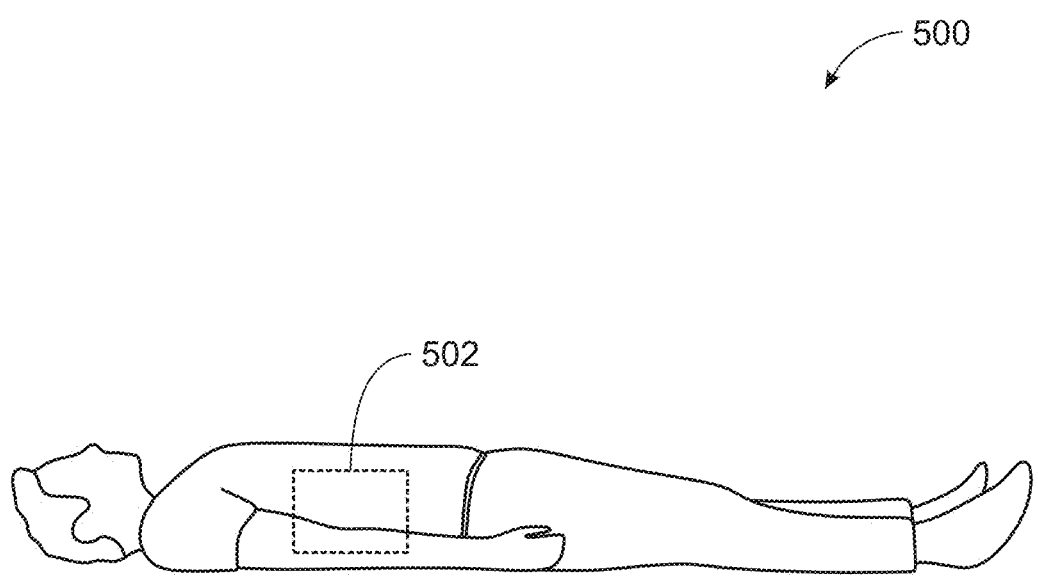
FIG. 5 is a schematic illustration of a patient from a side-view in accordance with an embodiment.
Figure 6:
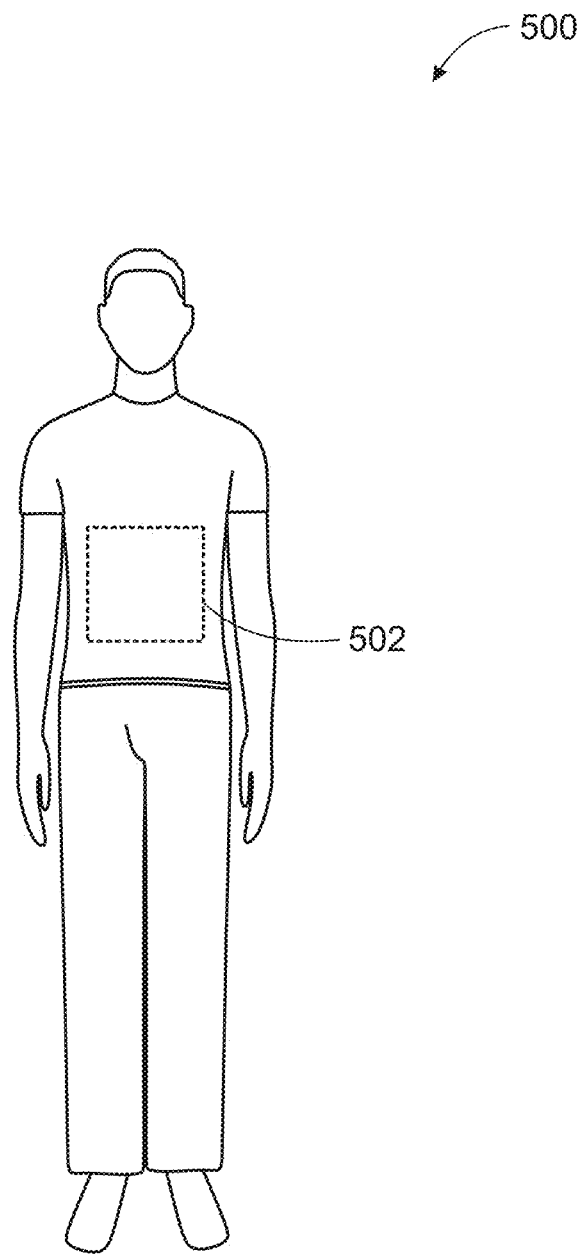
FIG. 6 is a schematic illustration of the patient from a top-view in accordance with an embodiment.

Next, at step 306, the processor 102 determines a visualization priority for each pixel in a joint-visualization image. The joint-visualization image includes a plurality of pixels. FIG. 5 represents a schematic illustration of a patient 500 from a side-view and FIG. 6 represents a schematic illustration of the patient 500 from a top-view. A volume-of-interest 502 is represented on both FIG. 5 and FIG. 6. The plurality of functional imaging datasets accessed by the processor 102 at step 302 have been acquired from the volume-of-interest 502 according to an exemplary embodiment. It should be appreciated that the plurality of imaging datasets may be acquired from a different volume-of-interest according to various embodiments. For example, the volume-of-interest may have a one or both of a different shape than the volume-of-interest 502 and/or be located in a different anatomical position with respect to the patient 500. Those skilled in the art will appreciate that the position of the volume-of-interest 500 will depend on the region or anatomy of the patient that is being imaged.

Figure 7:
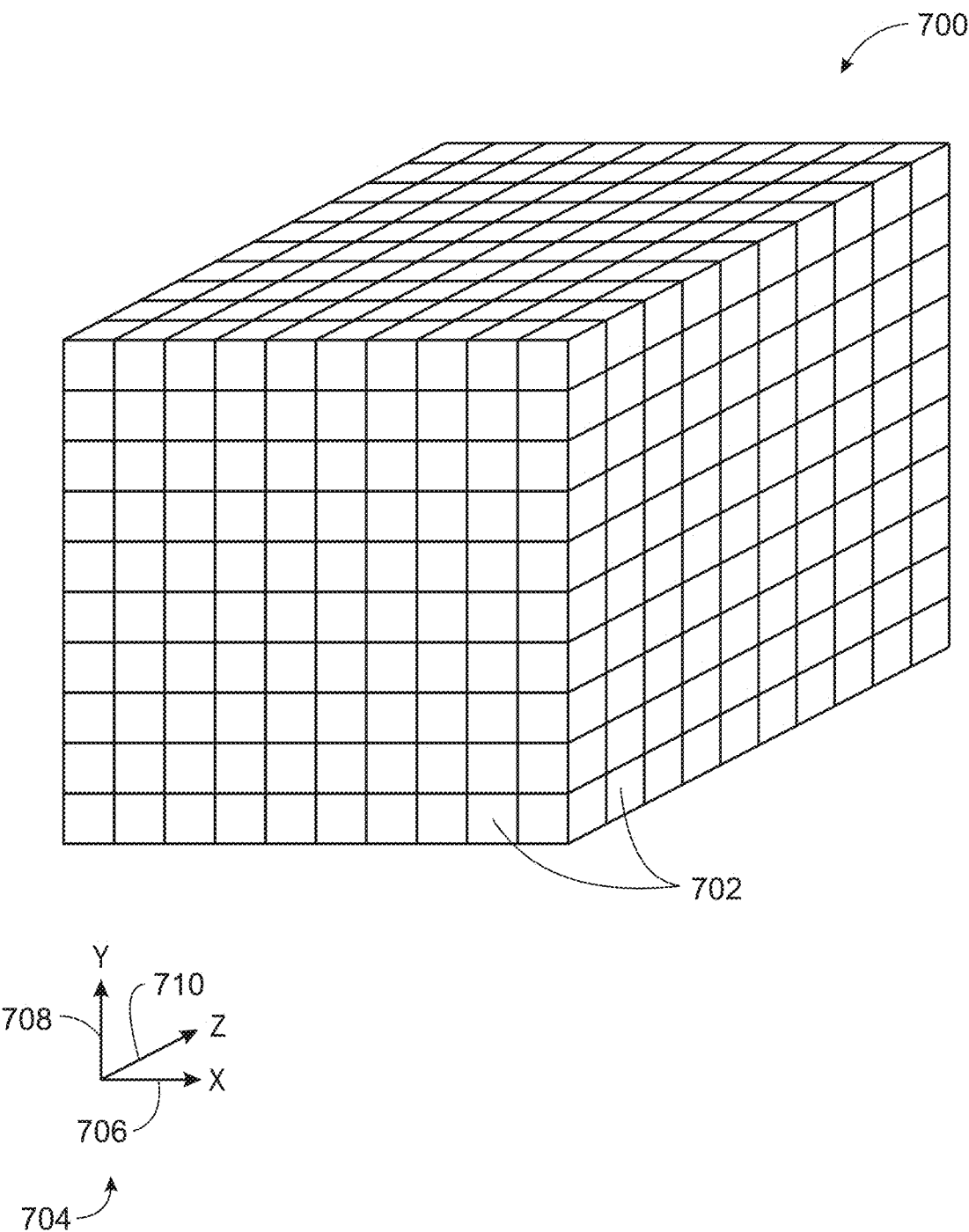
FIG. 7 is a schematic representation of a patient image volume in accordance with an embodiment.

FIG. 7 shows a representation of a patient image volume 700. According to an embodiment, the information in the patient image volume 700 may ultimately be rendered and displayed as a joint-visualization image. This technique may be used when, for example, rending and displaying a multiplanar reformation image. The patient image volume 700 includes a plurality of voxels 702. The patient image volume 700 is schematically represented as a 10×10×10 voxel cube, but it should be appreciated that the patient image volume for most applications will include significantly more voxels and that the patient image volume 700 is schematically represented as a 10×10×10 voxel cube to help explain various embodiments. FIG. 7 includes a coordinate axis 704 that represents an x-direction with an x-axis 706, a y-direction with a y-axis 708, and a z-direction with a z-axis 710.

At step 306, the processor 102 determines a visualization priority for each of the plurality of pixels within a joint-visualization image. The visualization priority defines which one of the plurality of functional imaging datasets will be represented by each of the plurality of pixels in the joint-visualization image. According to an embodiment of the method 300, each of the plurality of pixels in the joint-visualization image will represent information from only one of the plurality of functional imaging datasets. According to an embodiment, the processor 102 may individually determine, on a pixel-by-pixel basis, which one of the plurality of functional imaging datasets will be represented by each of the plurality of pixels in the joint-visualization image.

According to exemplary embodiments, the processor 102 may be configured to determine the visualization priority for each of the pixels based on a logical comparison of corresponding information from each of the plurality of functional imaging datasets. Corresponding information includes information from two or more of the functional imaging datasets that was acquired from within the same sub-volume within the volume-of-interest 502. For example, determining visualization priority based on a logical comparison of corresponding information may include comparing one or more first voxel values that are part of a first functional imaging dataset with one or more second voxel values that are part of a second functional imaging dataset. The first voxel values and the second voxel values may both have been acquired from the same sub-volumes within the volume-of-interest. For example, according to various embodiments, the corresponding information may include the portion of each functional imaging dataset that would be used to determine a value for a respective pixel. The number of voxel values used to determine the value of a single pixel may depend upon the type of image that is displayed. The value of each pixel may be based on a combination of multiple voxel values, a maximum or a minimum voxel value along a ray, or a single voxel value according to various embodiments.

As discussed previously with respect to the method 300, the functional imaging datasets may include quantitative data (including quantitative values) or non-quantitative data (including values that are not quantitative). According to some embodiments, one or more of the functional imaging datasets may be a quantitative dataset including quantitative values in physical units or according to standard calibrated scale. For example, the medical imaging system used to acquire the functional imaging dataset may calibrate the acquired data so that functional imaging dataset accessed by the processor 102 is a quantitative dataset. According to some embodiments where the acquired data is not calibrated by the medical imaging system, the processor 102 may be configured to convert the acquired data into quantitative data including calibrated values. For example, the processor 102 may convert one or more of the functional imaging datasets according to a standard calibrated scale, such as the standardized uptake value (SUV) scale. The standardized uptake value (SUV), which is also referred to as a dose uptake ratio, is the ratio of radiotracer concentration at a certain time normalized to injected does per unit of patient body mass. SUV is typically calculated using the following formula:

$$SUV = \frac{\text{Radiotracer Activity} \left(\frac{\text{MBq}}{\text{mL}}\right)}{\text{injected Dose (MBq)} / \left(\text{Patient mass (g)} \times 1 \left(\frac{\text{mL}}{\text{g}}\right)\right)}$$

The SUV scale provides an easy way to compare/evaluate measured functional imaging data with functional imaging data from previous studies. According to other embodiments, some or all of the plurality of functional imaging datasets may have already been converted into the SUV scale prior to being accessed by the processor 102 at step 302.

According to various embodiments, the processor 102 may determine the visualization priority for each pixel in the joint-visualization image by first determining a visualization priority for each of a plurality of voxels in a patient image space. This may be used, for example, when generating a multiplanar reformation image. According to an embodiment, the processor 102 may perform a logical comparison of the functional imaging data corresponding to each of the plurality of voxels using one or more logical rules stored in, for example, the memory 108. The logical rules may include one or more thresholds or conditions that collectively determine the functional imaging data type that will be represented by each of the voxels. For example, the logical rules may include one or more "if-then" logical conditions and/or thresholds that are used to determine the functional imaging data type that will be represented by each of the voxels. For example, the logical rules may include rules that indicate that each voxel should represent the functional imaging data type with the highest standard uptake value (SUV) value. Or the logical rules may include rules that are weighted towards one of the functional imaging data types. For example, the logical rules may apply a weighting factor (such as 0.25, 0.5, 0.75, 1.25, 1.5, 2, etc.) to values associated with one or more of the functional imaging data types and then determining that the voxel should represent the functional imaging data type with the highest value after scaling has been applied to the SUV value/s of one or more functional imaging data types. The logical rules may also include rules to establish priority between functional imaging datasets acquired with different imaging modalities. For example, the logical rules may establish one or more thresholds for determining the visualization priority when the plurality of functional imaging datasets were acquired with two or more different imaging modalities. For example, the logical rules may establish one or more thresholds to determine visualization priority between the various functional imaging data types acquired with different imaging modalities. The logical rules may establish rules or thresholds to determine which one of the functional imaging data types should be represented by each of the plurality of voxels. For example, the logical rules may establish a way to compare data from fMRI with SUV data acquired with a PET imaging system or a SPECT imaging system.

According to various exemplary embodiments, the setting of visualization priority for embodiments involving multiple modalities may involve a threshold, similar to the examples described previously, or it may involve a ratio of two values relative to one or more thresholds. For example, a threshold can be determined for SUV values for PET, or a threshold may be determined with respect to physical perfusion value for dynamic contract fMRI. The visualization priority may be based on one or more of the value (i.e., SUV physical perfusion value, etc.) or a ratio of two of the values. Additionally, the processor 102 may use a logical set of rules to establish visualization priority. According to an example involving both PET and fMRI, if the PET SUV value is above a first threshold, then PET (i.e., the PET functional imaging data type) may be assigned visualization priority. If the SUV value is below a second threshold and the perfusion is above a third threshold, then fMRI (i.e., the fMRI functional imaging data type) may be assigned visualization priority. It should be appreciated that this is just an exemplary embodiment and that any different logical rule or any different set of logical rules may be used to determine visualization priority. Additionally, while an example was described with respect to PET and fMRI, it should be appreciated that logical rules may be used to determine visualization priority for any two or more functional imaging data types according to various embodiments. The processor may be configured to determine the visualization priority for each of the plurality of pixels in the joint-visualization image differently according to various embodiments. For example, other embodiments may not involve determining a visualization priority for each of the plurality of voxels in a patient image volume. According to various other embodiments, the processor 102 may be configured to determine the visualization priority based on a logical comparison of corresponding voxel data from two or more of the functional imaging datasets. Additional details will be described hereinafter.

Figure 8:
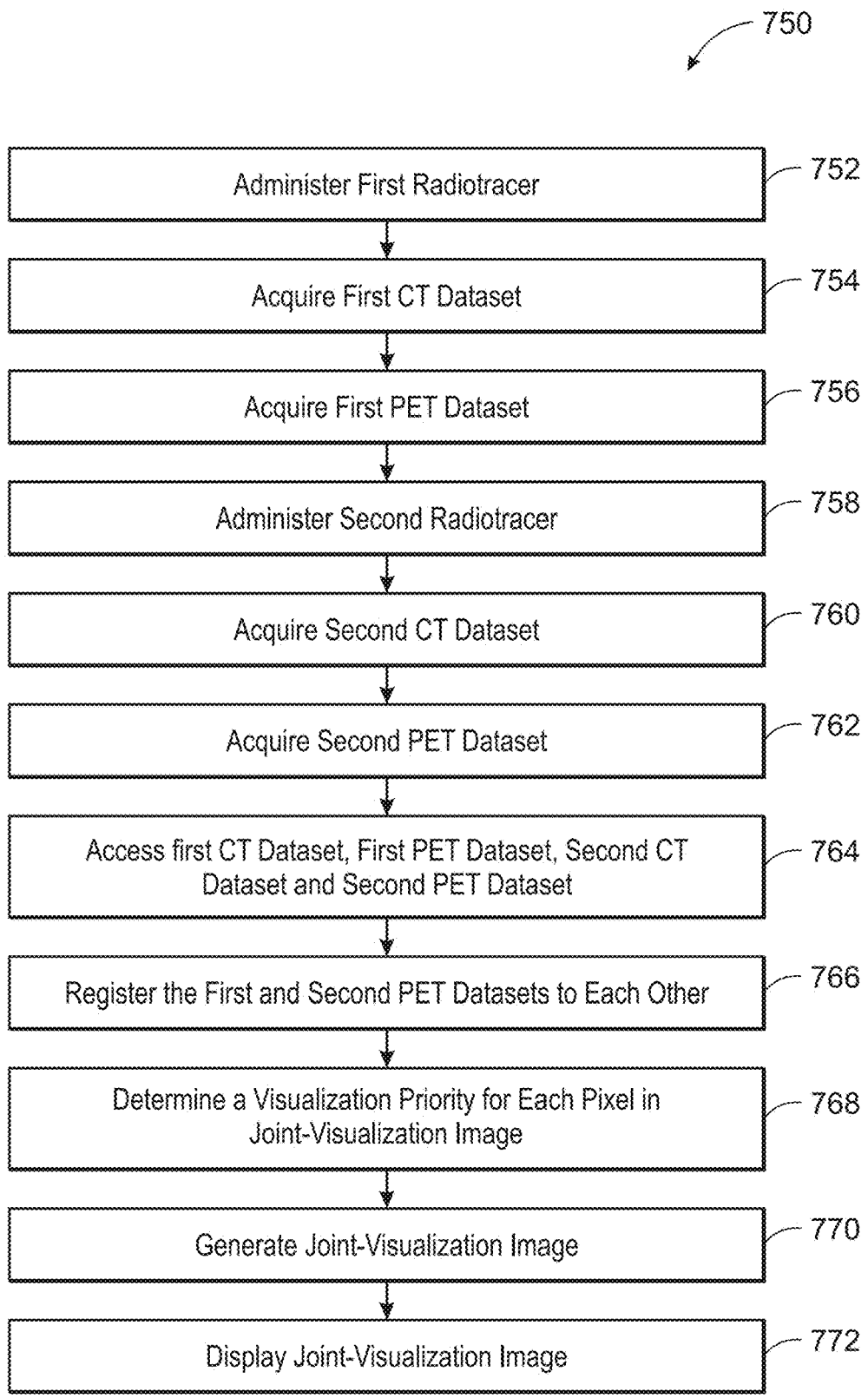
FIG. 8 is a flowchart of a method in accordance with an embodiment.

FIG. 8 illustrates a flowchart of an embodiment of a method 750. The technical effect of the method 750 is the display of joint-visualization image on the display device 106. The joint-visualization image represents information from a plurality of different functional imaging data types at the same time. Step 764, 766, 768, 770, and 772 of the method 750 may be performed with a workstation, such as the workstation 100 shown in FIG. 8.

At step 752, a clinician administers a first radiotracer to the patient. The first radiotracer includes a first ligand. According to an exemplary embodiment, the first radiotracer may be $^{68}$Ga-FAPI. At step 754, a first CT dataset of the patient is acquired. And at step 756, a first PET dataset is acquired from a volume-of-interest in the patient. Steps 754 and 756 may be performed with a PET-CT hybrid imaging system, for example.

Next, at step 758, the clinician administers a second radiotracer to the patient. The second radiotracer includes a second ligand. According to an exemplary embodiment, the second radiotracer may be $^{18}$F-FDG. According to various embodiments, it may be advantageous to use a first radiotracer with a higher specificity to the suspected disease. For example, depending upon the goal of the study, $^{68}$Ga-FAPI may have a higher specificity to the suspected disease than $^{18}$F-FDG. Since there are no other radiotracers in the patient when the first radiotracer is administered, the measured signals (i.e., counts) from the first radiotracer are always accurate. However, the signals (i.e., counts) from the second radiotracer are inherently less accurate than the signals (i.e., counts) from the first radiotracer. This is because the signals (i.e., counts) detected after the second radiotracer has been administered are due to both the remaining active portions of the first radiotracer and the second radiotracer. It is important that there is sufficient time gap between step 752, when the first radiotracer is administered, and step 758, when the second radiotracer is administered to the patient in order to make it easier to differentiate the effects of the first radiotracer from those of the second radiotracer since the gamma photons detected by the PET detector are all of the same energy (511 keV). According to an exemplary embodiment, the clinician may wait approximately 1 hour between administering the first radiotracer at step 752 and administering the second radiotracer at step 758. It should be appreciated that at different amount of time between the administration of the first radiotracer and the second radiotracer may be used according to various embodiments.

The second radiotracer includes a different ligand than the first radiotracer. As discussed above, the ligand used in a particular radiotracer determines the proteins with which the radiotracer interacts. As such, imaging the patient with multiple different radiotracers (each with a unique ligand) may provide different clinician insights regarding the functional activity of the patient.

After the second radiotracer has been administered at step 758, a second CT dataset is acquired at step 760. A second PET dataset is acquired at step 762. The second CT dataset may be a full CT dataset, or the second CT dataset may be a low-dose CT dataset. The second CT dataset and the second PET dataset may be acquired using the same PET-CT hybrid imaging system that was used previously.

Next, at step 764, a processor, such as the processor 102 in the workstation 100 accesses the first CT dataset, the first PET dataset, the second CT dataset, and the second PET dataset. According to an embodiment, the first CT dataset may be registered to the first PET dataset and the second CT dataset may be registered to the second PET dataset since the first PET dataset and the first CT dataset were acquired on the PET-CT hybrid imaging system during a single session, and the second PET dataset and the second CT dataset were acquired on the PET-CT hybrid imaging system during a single session. As is known by those skilled in the art, the PET dataset and the CT dataset acquired on a hybrid imaging system are at a fixed spatial displacement from each other, which is easy to determine based on the geometry of the hybrid imaging system. The processor 102 may register the first CT dataset to the first PET dataset and the second CT dataset to the second PET dataset. Or, according to other embodiments, the PET-CT hybrid imaging system may register the first CT dataset to the first PET dataset and the second CT dataset to the second PET dataset.

At step 766, the processor 102 registers the first PET dataset to the second PET dataset. According to an exemplary embodiment, the processor 102 may perform the registration by registering the first CT dataset to the second CT dataset. Since the first PET dataset is registered to the first CT dataset and the second PET dataset is registered to the second CT dataset, the processor 102 may register the first PET dataset to the second PET dataset by registering the first CT dataset to the second CT dataset. According to one embodiment, the processor 102 may determine any translations, rotations, and/or deformations necessary to register that first CT dataset to the second CT dataset and use the determined translations, rotations, or deformations to register the first PET dataset to the second PET dataset. According to other embodiments that do not include anatomical imaging datasets, such as the first CT dataset or the second CT dataset, the processor 102 may directly register the plurality of functional imaging datasets to each other using the information in each respective functional imaging dataset.

Figure 9:
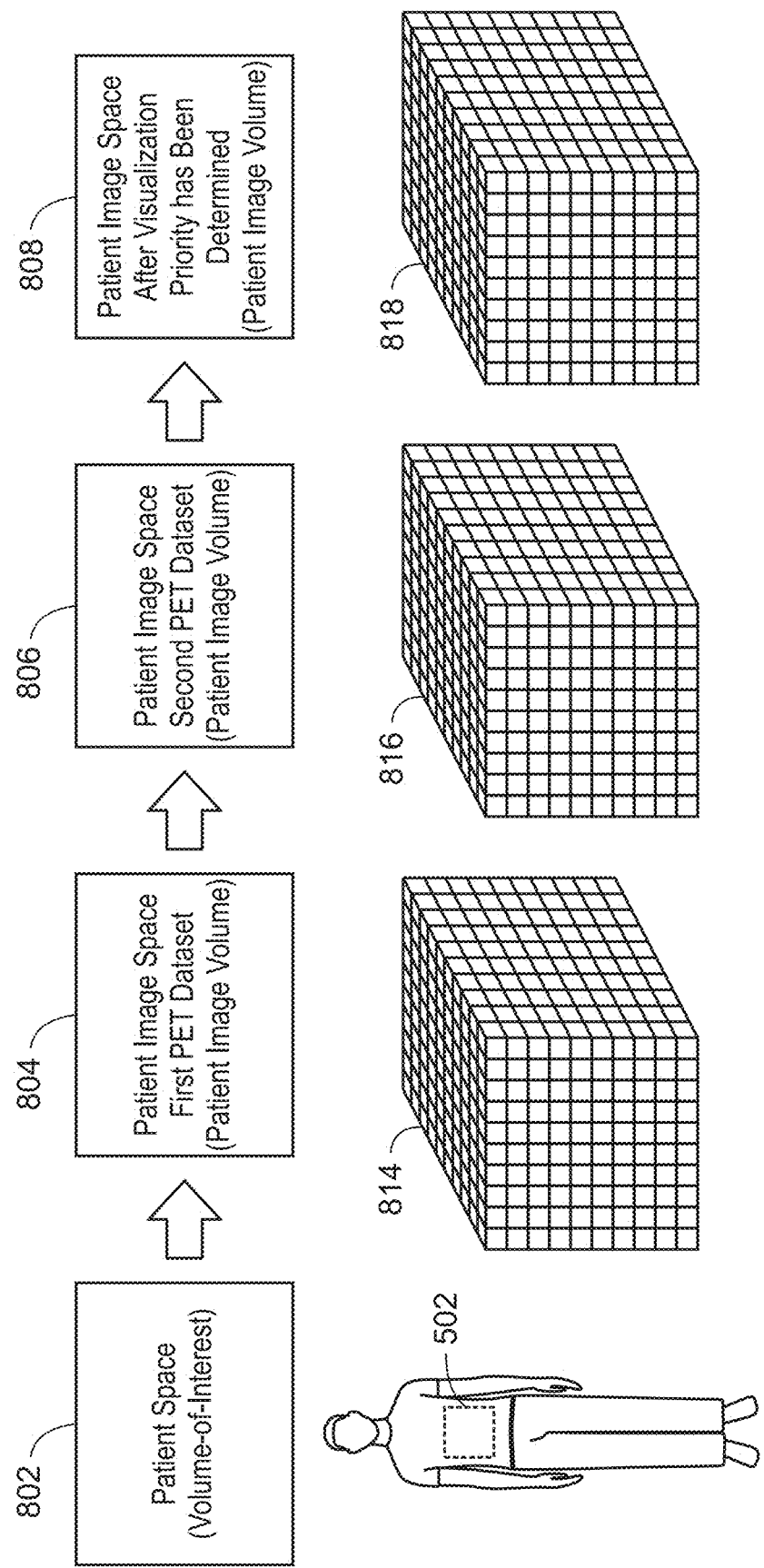
FIG. 9 is a schematic representation of a portion of a method in accordance with an embodiment.

FIG. 9 is a schematic representation of a portion of the method 750 according to an embodiment. FIG. 9 includes a first block 802, a second block 804, a third block 806, and a fourth block 808. The first block 802 represents a patient space. The volume-of-interest 502 is within the patient space, and both the first PET dataset and the second PET dataset were acquired from the volume-of-interest 502. The second block 804 represent a patient image space. The patient image volume is within the patient image space. For purposes of this disclosure, the plurality of voxels representing the volume-of-interest are considered as being in the patient image space. According to the exemplary method represented in FIG. 9, two functional imaging datasets were acquired: the first PET dataset; and the second PET dataset. Patient image volume 814 is a schematic representation of the voxel data from the first PET dataset acquired from within the volume-of-interest. In other words, each of the voxels in the patient image volume 814 represents information acquired during step 756 (i.e., information from the first PET dataset) corresponding to a distinct sub-volume within the volume-of-interest. The third block 806 represents the patient image space. The patient image volume is within the patient image space. For purposes of this disclosure, the plurality of voxels representing the volume-of-interest are considered as being in the patient image space. Patient image volume 816 is a schematic representation of the voxel data from the second PET dataset acquired from within the volume-of-interest 502. In other words, each of the voxels in the patient image volume 816 represents information acquired during step 762 (i.e., information from the second PET dataset) corresponding to a distinct sub-volume within the volume-of-interest. Since the first PET dataset and the second PET dataset were both acquired from the same volume-of-interest, those skilled in the art should appreciate that there are two values associated with each voxel location: a first voxel value corresponding to the first PET dataset; and a second voxel value corresponding to the second PET dataset.

Next, at step 768, the processor 102 determines a visualization priority for each pixel in a joint-visualization image. The patient image volume is a representation of the volume-of-interest in the patient image space. According to an embodiment, there are two different functional imaging data values for each voxel within the patient image volume: a first value corresponding to the first PET dataset and a second value corresponding to the second PET dataset. In other words, each voxel corresponds to a specific sub-volume within the patient image volume. And two different functional imaging data values were acquired from each sub-volume within the patient image volume. Therefore, there are two different functional image data values for each voxel. According to other embodiments, which may include three or more functional imaging data values for each voxel within the patient image volume, there would be three or more functional imaging data values for each voxel within the patient image volume. Therefore, it may be necessary to determine a visualization priority for each of the voxels within the patient image volume. According to an embodiment, determining the visualization priority for each pixel may include individually determining, for each voxel in the patient image space, if the voxel should represent a first value from the first PET dataset (i.e., representing a first functional imaging data type) or a second value from the second PET dataset (i.e., representing a second functional imaging data type). The processor 102 may determine the visualization priority based on a comparison of the information from each of the plurality of functional imaging datasets using a set of logical rules stored in the memory 108.

According to an exemplary embodiment, the first PET dataset may have been acquired with $^{68}$Ga-FAPI as the first radiotracer and the second PET dataset may have been acquired with $^{18}$F-FDG. It should be appreciated that $^{68}$Ga-FAPI and $^{18}$F-FDG are merely exemplary radiotracers and that the method may use any other PET radiotracers including different ligands according to various embodiments. According to some embodiments, one or more of the functional imaging datasets may be a quantitative dataset including quantitative values in physical units or according to standard calibrated scale. For example, the medical imaging system used to acquire the functional imaging dataset may calibrate the acquired data so that functional imaging dataset accessed by the processor 102 is a quantitative dataset. According to some embodiments where the acquired data is not calibrated by the medical imaging system, the processor 102 may be configured to convert the acquired data into quantitative data including calibrated values. The processor 102 may convert one or more of the functional imaging datasets according to a standard calibrated scale, such as the standardized uptake value (SUV) scale. For example, the processor 102 may first convert the first PET dataset and the second PET dataset to a quantitative scale, such as the SUV scale. According to an exemplary embodiment, the processor 102 may convert the first PET dataset to a first SUV scale and the processor 102 may convert the second PET dataset to a second SUV scale. The first SUV scale may be generated based on the first administered dose and the measurements obtained when acquiring the first functional imaging dataset. Since the first radiotracer is the only radiotracer in the patient's body at the time when the first functional imaging dataset is being acquired, the calculation of the first SUV scale is a relatively easy. Calculating the second SUV scale for the second radiotracer is not as straight-forward since the detected signals are due to both the first radiotracer, which was administered earlier, and the second radiotracer. The processor 102 needs to calculate an estimate of the dose remaining from the administration of the first radiotracer ($^{68}$Ga-FAPI), as gamma rays from both the first radiotracer and the second radiotracer ($^{18}$F-FDG) will be detected by the detector of the PET imaging system.

The processor 102 may implement an equation or algorithm to estimate the amount of contribution from first radiotracer ($^{68}$Ga-FAPI). The equation or algorithm may estimate the contribution based on factors, such as the amount of the first radiotracer ($^{68}$Ga-FAPI) administered to the patient, an estimated rate of accumulation of the first radiotracer in organs or lesions in the patient's body, and the half-life of the first radiotracer ($^{68}$Ga-FAPI). The processor 102 may access one or more look-up tables stored in the memory 108 in order to obtain one or more of the estimated rate of accumulation of the first radiotracer ($^{68}$Ga-FAPI) or the half-life of the first radiotracer ($^{68}$Ga-FAPI). In order to calculate the contribution from the second radiotracer ($^{18}$F-FDG), the processor 102 may subtract the estimated contribution from the first radiotracer ($^{68}$Ga-FAPI) from the signals acquired by the detector after the administration of the second radiotracer ($^{18}$F-FDG). Since the contribution from the second radiotracer ($^{18}$F-FDG) cannot be measured directly, and because the contributions from the first radiotracer ($^{68}$Ga-FAPI) need to be estimated in order to calculate an estimated contribution of the second radiotracer ($^{18}$F-FDG), the measurements associated with the second functional imaging dataset and the SUV scale for the second functional imaging dataset are inherently less accurate than the measurements associated with the first functional imaging dataset and the SUV scale for the first functional imaging dataset. For these and other reasons, administering the most specific of the plurality of radiotracers to the patient first may be advantageous since the signals obtained from the first radiotracer will always be the most accurate when dealing with clinical situations that ultimately involve having multiple PET radiotracers in the patient at the same time. As discussed hereinabove, the SUV scale for each radiotracer may be calculated independently according to an exemplary embodiment.

After converting the first functional imaging dataset and the second functional imaging dataset to the SUV scale, the processor 102 may determine the visualization priority for each voxel based on the SUV values of the first and second functional imaging datasets. As discussed previously with respect to FIG. 9, patient image volume 814 is a schematic representation of the voxel data from the first PET dataset acquired from within the volume-of-interest. Patient image volume 816 is a schematic representation of the voxel data from the second PET dataset acquired from within the volume-of-interest 502. There are two values associated with each voxel location: the voxel value corresponding to the first PET dataset; and the voxel value corresponding to the second PET dataset.

According to an embodiment, determining the visualization priority includes individually determining, for each voxel in the patient image volume 818, if the voxel should represent the first PET value (i.e., representing a first functional imaging data type) or the second PET value (i.e., representing a second functional imaging data type). The processor 102 may be configured to determine the visualization priority by applying logical rules stored in the memory 108. As discussed earlier, the logical rules may establish rules or thresholds to determine which one of the functional imaging data types should be represented by each of the plurality of voxels. According to an embodiment, the processor 102 may assign visualization priority to the functional imaging data type with the highest SUV value. For example, each voxel in the patient image space may represent information from the functional imaging dataset with the highest SUV value. As described above, there are two different functional imaging data values for each voxel within the patient image volume: a first PET value (from the first PET dataset) and a second PET value (from the second PET dataset). The first PET value may be converted to a first SUV value and the second PET value may be converted to a second SUV value. The processor 102 could then determine if the first SUV value or the second SUV is greater. According to an embodiment, the processor 102 would then assign visualization priority to the functional imaging data type associated with the higher SUV value. For example, if, for a voxel, the first SUV value ($^{68}$Ga-FAPI) is higher than the second SUV value ($^{18}$F-FDG), then that particular voxel would be assigned a visualization priority of the first functional imaging data type (associated with the first functional imaging dataset). For another voxel, if the second SUV value ($^{18}$F-FDG) is higher than the first SUV value ($^{68}$Ga-FAPI), then the processor 102 would assign a visualization priority of the second functional imaging data type (associated with the second functional imaging dataset) for that particular voxel. The processor 102 may proceed to individually assign visualization priorities to each of the voxel in the patient imaging space according to the method described hereinabove.

According to another embodiment, the processor 102 may be configured to apply a weighting factor to one or more of the functional imaging data types in order to emphasis one or more of the plurality of data types. For example, the logical rules stored in the memory 108 may include a weighting factor that is applied to one or more of the functional imaging data types. For example, the logical rules may emphasize one of the functional imaging data types by one or both of applying a weighting factor of greater than 1 (such as 1.25, 1.5, 1.75, etc.) to the SUV values from one of the functional imaging datasets to emphasize that functional imaging data type associated with the one of the functional imaging datasets; or applying a weighting factor of less than 1 (such as 0.25, 0.5, 0.75, etc.) to another of the functional imaging data types associated with a different one of the functional imaging datasets. For example, to emphasize the first functional imaging data type, associated with the first functional imaging dataset ($^{68}$Ga-FAPI), the weighting factor may include one or both of applying a weighting factor of greater than 1 to the SUV values generated from the first functional imaging dataset ($^{68}$Ga-FAPI) or applying a weighting factor of less than 1 to the SUV values generated form the second functional imaging dataset ($^{18}$F-FDG). After applying the one or more weighting factors, weighted SUV data including weighted SUV values is created. According to an exemplary embodiment, the processor 102 may assign visualization priority to each of the plurality of voxels by selecting the functional imaging data type associated with the functional imaging dataset with the highest weighted SUV value. The embodiment described above would weight the first functional imaging data type associated with the first functional imaging dataset ($^{68}$Ga-FAPI) more strongly than the second functional imaging data type associated with the second functional imaging dataset ($^{18}$F-FDG). This may be desirable according to various embodiments because $^{68}$Ga-FAPI has a greater specificity as a radiotracer than $^{18}$F-FDG. According to other embodiments, the logical rules may be configured to weigh one or more different functional imaging data types. For example, the second functional imaging data type, associated with the second functional imaging dataset ($^{18}$F-FDG) may be weighted more strongly than the first functional imaging data type associated with the first functional imaging dataset ($^{68}$Ga-FAPI). In FIG. 9, the patient image volume 818 represents the plurality of voxels after the visualization priority has been determined for each of the plurality of voxels. In other words, in the patient volume 818, each of the plurality of voxels has a visualization priority that is associated with only one of either the first functional imaging data type or the second functional imaging data type. This means that each of the voxels represents information from only one of the first functional imaging dataset or the second functional imaging dataset. The various functional imaging data types may be weighted differently according to other embodiments.

While the embodiment above described a technique for determining visualization priority based on SUV values, according to other embodiments, the processor 102 may be configured to determine the visualization priority for each of the plurality of voxels based on absolute activity from the region within the patient's volume-of-interest corresponding to each of the plurality of voxels. For example, the visualization priority for each of the plurality of voxels in the patient image space may be determined by comparing the absolute activity level of the first functional imaging data type to the absolute activity level of the second functional imaging data type. As with the previous embodiment, the logical rules stored in the memory 108 may include a weighting factor that is applied to data from one or more of the functional imaging data types.

While the embodiments described above were specific to an embodiment with two functional imaging data types (i.e., a first functional imaging dataset acquired with $^{68}$Ga-FAPI and a second functional imaging dataset acquired with $^{18}$F-FDG), other embodiments may have three or more different functional imaging data types. For example, additional functional imaging datasets may be accessed by the processor 102. According to an embodiment, a unique radiotracer, including a ligand that is unique from the ligands in the other radiotracers may be administered to the patient before the acquisition of each additional functional imaging dataset. Those skilled in the art will appreciate that, for PET imaging, accurately differentiating the effects of radiotracers administered to the patient while two or more previously-applied radiotracers are still in the patient's body may be less accurate than embodiments using two or fewer distinct radiotracers. According to various embodiments, the processor 102 may use the visualization priority that was determined for the voxels in the patient image volume in order to determine the visualization priority for each of the plurality of pixels in the joint-visualization image. This may be used, for example, when the joint-visualization image is a multiplanar reformation image. The processor may be configured to determine the visualization priority for each of the plurality of pixels in the joint-visualization image differently according to various embodiments. For example, other embodiments may not involve determining a visualization priority for each of the plurality of voxels in a patient image volume. According to various other embodiments, the processor 102 may be configured to determine the visualization priority for each of the plurality of pixels in the joint-visualization image based on a logical comparison of corresponding voxel data from corresponding locations from two or more of the functional imaging datasets. Additional details will be described hereinafter.

Figure 11:
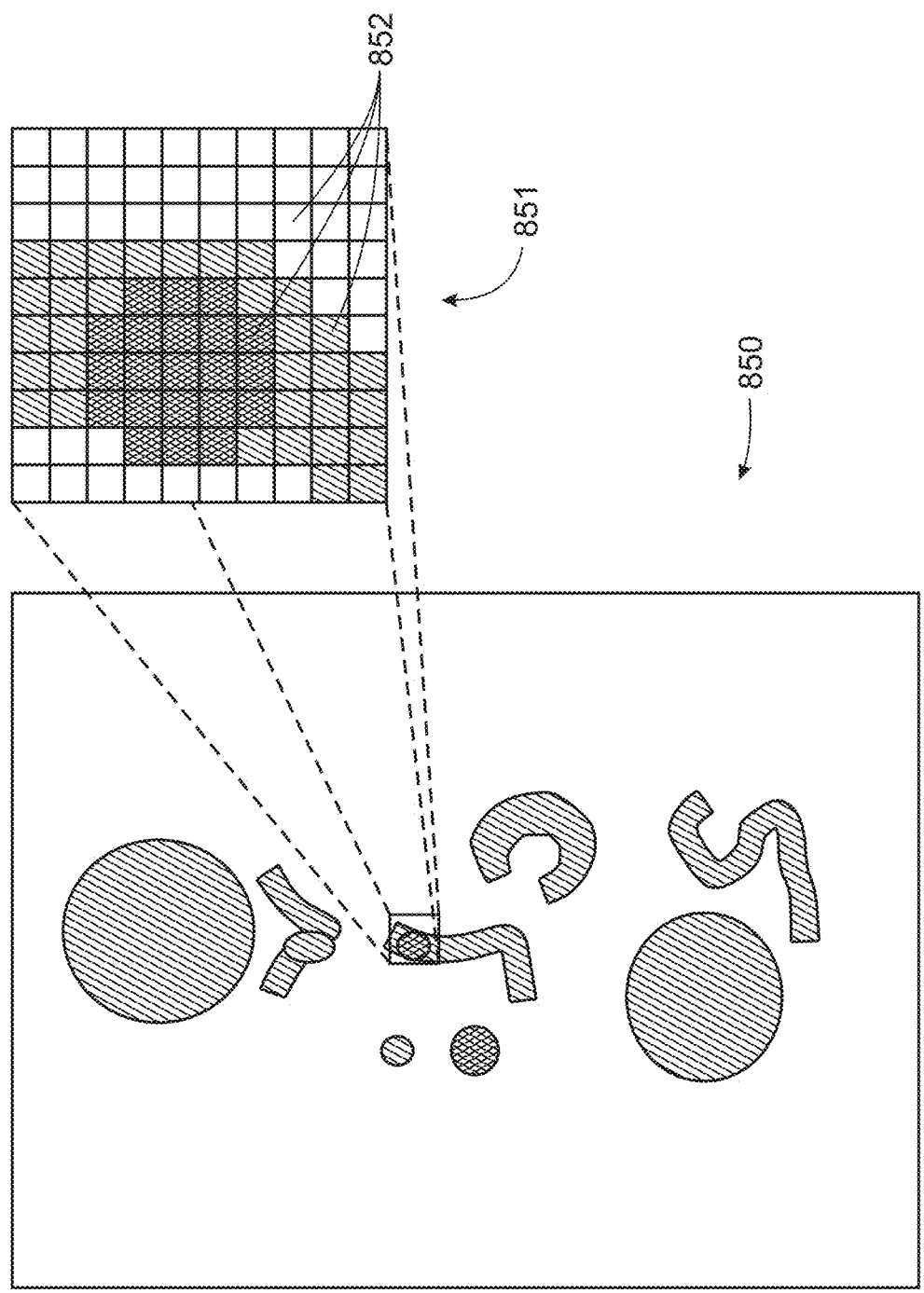
FIG. 11 a representation of a joint-visualization image in accordance with an embodiment.

Referring back to FIG. 8, at step 770, the processor 102 generates a joint-visualization image after determining the visualization priority for each of the plurality of pixels in the patient image volume 818. According to various embodiments, the processor 102 may generate the joint-visualization image by generating a rendering based on the patient image volume. FIG. 11 shows a representation of a joint-visualization image 850. The joint-visualization image 850 may be generated based on a rendering using the voxels in the patient image volume 818 according to an embodiment. Next, at step 772, the processor 102 displays the joint-visualization image on the display device, such as the display device 106. FIG. 11 includes a magnified portion 851. The magnified portion 851 includes a representation of a plurality of pixels 852 used to display the joint-visualization image 850. A subset of the plurality of pixels 852 are shown schematically shown with cross-hatching in FIG. 11. Each pixel illustrated with cross-hatching represents the first functional imaging data type (i.e., a value from the first functional imaging dataset), and each pixels shown with hatching represents the second functional imaging data type (i.e., a value from the second functional imaging dataset).

Figure 10:
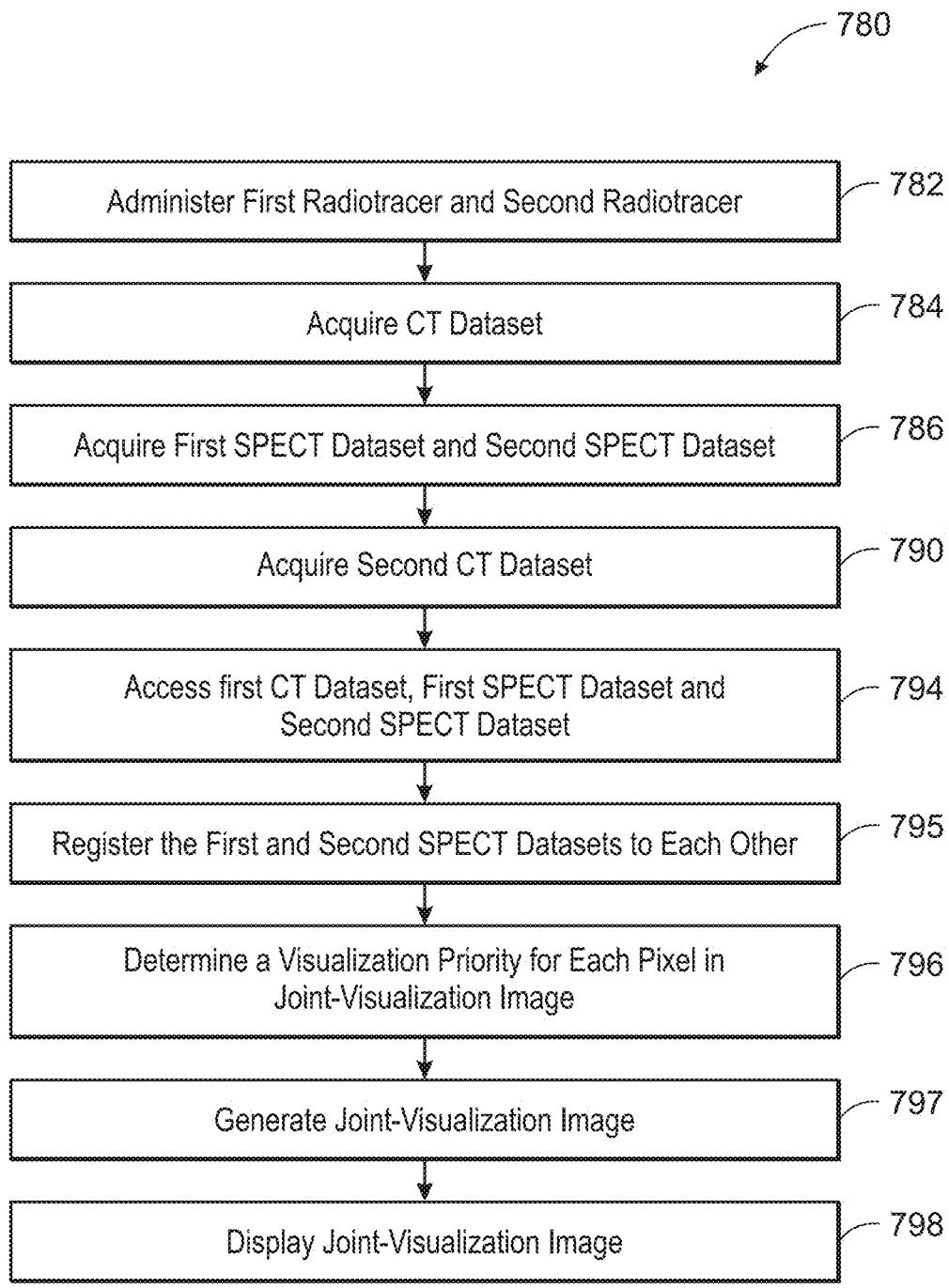
FIG. 10 is a flowchart of a method in accordance with an embodiment.

FIG. 10 illustrates a flowchart of an embodiment of a method 780. The technical effect of the method 750 is the display of joint-visualization image on the display device 106. The joint-visualization image represents information from a plurality of functional imaging data types at the same time. Steps 794, 795, 796, 797, and 798 of the method 750 may be performed with a workstation, such as the workstation 100 shown in FIG. 8.

At step 782, a clinician administers a first radiotracer and a second radiotracer to the patient. The first radiotracer includes a first ligand. The second radiotracer includes a second ligand that is different than the first ligand. According to an exemplary embodiment, the first radiotracer may be iodine-123 and the second radiotracer may be technetium-99m. At step 784, the clinician acquires a CT dataset of the patient. At step 786, the clinician acquires a first SPECT and second SPECT dataset from the volume of interest within the patient. Steps 784 and 786 may be performed with a SPECT-CT hybrid imaging system, for example. The clinician may administer the second radiotracer to the patient immediately after the first radiotracer since it is possible to distinguish signals emitted from the first radiotracer from signals emitted from the second radiotracer when performing SPECT imaging. According to other embodiments, there may be a period of time between the administration of the first radiotracer and the administration of the second radiotracer.

The second radiotracer includes a different ligand than the first radiotracer. As discussed above, the ligand used in a particular radiotracer determines the proteins with which the radiotracer interacts. As such, imaging the patient with multiple different radiotracers (each with a unique ligand) may provide different clinician insights.

Next, at step 794, a processor, such as the processor 102 in the workstation 100 accesses the first CT dataset, the first SPECT dataset, and the second SPECT dataset. The workstation may, for instance, access the datasets (i.e., the first CT dataset, the first SPECT dataset, and the second SPECT dataset) from a memory or storage, from a Picture archiving and communication system (PACS), from a local server, from a remote server, or directly from one or more imaging systems, such as the SPECT-CT imaging system. According to an embodiment, the first CT dataset may be registered to both the first SPECT dataset and the second SPECT dataset since both SPECT datasets and the CT dataset were acquired on the SPECT-CT hybrid imaging system during a single session. As is known by those skilled in the art, the SPECT datasets and the CT dataset acquired on a hybrid imaging system are at a fixed spatial displacement from each other, which is easy to determine based on the geometry of the hybrid imaging system. According to other embodiments, the each of the two or more SPECT datasets may be acquired during a separate acquisition.

At step 795, the processor 102, registers the first SPECT dataset to the second SPECT dataset. According to an exemplary embodiment where the first SPECT dataset and the second SPECT dataset are acquired on the same hybrid imaging system, the first and second SPECT datasets may be very easy to register since they were both acquired with the same hybrid system over the same period of time. According to other embodiments, the hybrid imaging system may register the first SPECT dataset to the second SPECT dataset during or after the acquisition of the first and second SPECT datasets.

Next, at step 796, the processor 102 determines a visualization priority for each pixel in a joint-visualization image. The patient image volume is a representation of the volume-of-interest in the patient image space. There are two different functional imaging data values for each voxel within the patient image volume: a first SPECT value from the first SPECT dataset and a second SPECT value from the second SPECT dataset. According to other embodiments, which may include three or more functional imaging data values for each voxel within the patient image volume, there would be three or more functional imaging data values for each voxel within the patient image volume. Therefore, it may be necessary to determine a visualization priority for each of the voxels within the patient image volume. According to an embodiment, determining the visualization priority for each pixel may include individually determining, for each voxel in the patient image space, if the voxel should represent the first SPECT value (i.e., representing a first functional imaging data type) or the second SPECT value (i.e., representing a second functional imaging data type). The processor 102 may then determine the visualization priority for each pixel based on a logical comparison of the information from each of the plurality of functional imaging datasets using a set of logical rules stored in the memory 108. As discussed above, the processor 102 may identify a visualization priority for each of the plurality of pixels in the joint-visualization image based on a logical comparison of corresponding information in each of the plurality of functional imaging datasets. The visualization priority determines which one of the plurality of functional imaging datasets is represented by each of the plurality of pixels in the joint-visualization image.

According to an exemplary embodiment, the first SPECT dataset may have been acquired with $^{123}$I-sodium-iodide as the first radiotracer and the second SPECT dataset may have been acquired with $^{99m}$Tc-tetrofosmin. According to an embodiment, $^{99m}$Tc-tetrofosmin and $^{123}$I-sodium-iodide can be used simultaneously for the imaging of thyroid-related diseases, for example. In such cases, $^{123}$I-sodium-iodide can have higher specificity than the $^{99m}$Tc-tetrofosmin, but the $^{99m}$Tc-tetrofosmin can highlight additional relevant tissue/process types with lower iodine uptake. It should be appreciated that $^{123}$I-sodium-iodide and $^{99m}$Tc-tetrofosmin are merely exemplary radiotracers and that the method may use any other SPECT radiotracers with different ligands according to various embodiments. According to some embodiments, one or more of the functional imaging datasets may be a quantitative dataset including quantitative values in physical units or according to standard calibrated scale. For example, the medical imaging system used to acquire the functional imaging dataset may calibrate the acquired data so that functional imaging dataset accessed by the processor 102 is a quantitative dataset. According to some embodiments where the acquired data is not calibrated by the medical imaging system, the processor 102 may be configured to convert the acquired data into quantitative data including calibrated values. For example, the processor 102 may convert one or more of the functional imaging datasets according to a standard calibrated scale, such as the standardized uptake value (SUV) scale. For example, the processor 102 may first convert the first SPECT dataset and the second SPECT dataset to a quantitative scale, such as the SUV scale, or any other quantitative scale. According to an exemplary embodiment, the processor 102 may convert the first SPECT dataset to a first SUV scale and the processor 102 may convert the second SPECT dataset to a second SUV scale. The first SUV scale may be generated based on the first administered dose and the measurements obtained while acquiring the first functional imaging dataset. The second SUV scale may be generated based on the second administered dose and the measurements obtained while acquiring the second functional imaging dataset. According to other embodiments, the first SPECT dataset and the second SPECT dataset may be represented using an arbitrary scale. The arbitrary scale may, for instance, be determined by the image generation process and or imaging parameters.

In both PET and SPECT functional imaging, the functional imaging data within one or more of the functional imaging datasets may be provided in physical activity concentration (MBq/mL) or in SUV. In some cases, the reconstructed images may be given in an arbitrary scale if all the calibration parameters are not known. Functional MRI (fMRI) can show several different types of physiological processes. As in PET and SPECT, the image data may be in quantitative or non-quantitative scales. For example, in dynamic contrast-enhanced imaging with a Gadolinium agent, which may be used to analyze blood-in-tissue perfusion and permeability, image data may be provided in quantitative physical units of flow rate or related physical parameters. Similar to MRI, dynamic contrast-enhanced imaging is a technique used in functional CT imaging with Iodine contrast agent. In MRI, there are techniques for functional imaging even without using Gadolinium contrast agent. The methods described herein may be used with either quantitative or non-quantitative functional imaging datasets.

Referring back to FIG. 10, after converting the first functional imaging dataset and the second functional imaging dataset to the SUV scale, the processor 102 may determine the visualization priority for each voxel based on the SUV values of the first and second functional imaging datasets. As discussed previously, there are two values associated with each voxel location: the voxel value corresponding to the first SPECT dataset; and the voxel value corresponding to the second SPECT dataset.

According to an embodiment, determining the visualization priority for each pixel may include individually determining, for each voxel in the patient image volume, if the voxel should represent the first SPECT value (i.e., representing a first functional imaging data type) or the second SPECT value (i.e., representing a second functional imaging data type). The processor 102 may be configured to determine the visualization priority by applying logical rules stored in the memory 108. As discussed earlier, the logical rules may establish rules or thresholds to determine which one of the functional imaging data types should be represented by each of the plurality of voxels. According to an embodiment, the processor 102 may assign visualization priority to the functional imaging data type with the highest SUV value. For example, each voxel in the patient image space may represent information from the functional imaging dataset with the highest SUV value. As described above, there are two different functional imaging data values for each voxel within the patient image volume: a first SPECT value and a second SPECT value. The first SPECT value is converted to a first SUV value and the second SPECT value is converted to a second SUV value. The processor could then determine if the first SUV value or the second SUV is greater. According to an embodiment, the processor 102 would then assign visualization priority to the functional imaging data type associated with the higher SUV value. For example, if, for a voxel, the first SUV value ($^{123}$I-sodium-iodide) is higher than the second SUV value ($^{99m}$Tc-tetrofosmin), then that particular voxel would be assigned a visualization priority of the first functional imaging data type (associated with the first functional imaging dataset). For another voxel, if the second SUV value ($^{99m}$Tc-tetrofosmin) is higher than the first SUV value ($^{123}$I-sodium-iodide), then the processor 102 would assign a visualization priority of the second functional imaging data type (associated with the second functional imaging dataset). The processor 102 may proceed to individually assign visualization priorities to each of the voxel in the patient imaging space according to the method described hereinabove.

According to another embodiment, the processor 102 may be configured to apply a weighting factor to one or more of the functional imaging data types in order to emphasis one or more of the plurality of data types. For example, the logical rules stored in the memory 108 may include a weighting factor that is applied to one or more of the functional imaging data types. For example, the logical rules may emphasize one of the functional imaging data types by one or both of applying a weighting factor of greater than 1 (such as 1.25, 1.5, 1.75, etc.) to the SUV values from one of the functional imaging datasets to emphasize that functional imaging data type associated with the one of the functional imaging datasets; or applying a weighting factor of less than 1 (such as 0.25, 0.5, 0.75, etc.) to another of the functional imaging data types associated with a different one of the functional imaging datasets. For example, to emphasize the first functional imaging data type, associated with the first functional imaging dataset ($^{123}$I-sodium-iodide), the weighting factor may include one or both of applying a weighting factor of greater than 1 to the SUV values generated from the first functional imaging dataset ($^{123}$I-sodium-iodide) or applying a weighting factor of less than 1 to the SUV values generated form the second functional imaging dataset ($^{99m}$Tc-tetrofosmin). After applying the one or more weighting factors, weighted SUV data, including weighted SUV values, is created. According to an exemplary embodiment, the processor 102 may assign visualization priority to each of the plurality of voxels by selecting the functional imaging data type associated with the functional imaging dataset with the highest weighted SUV value. The embodiment described above would weight the first functional imaging data type associated with the first functional imaging dataset ($^{123}$I-sodium-iodide) more strongly than the second functional imaging data type associated with the second functional imaging dataset ($^{99m}$Tc-tetrofosmin). This may be desirable according to various embodiments because $^{123}$I-sodium-iodide may have a greater specificity as a radiotracer than $^{99m}$Tc-tetrofosmin for certain clinical applications, such as the imaging of thyroid-related diseases. According to other embodiments, the logical rules may be configured to weight one or more different functional imaging data types. For example, the second functional imaging data type, associated with the second functional imaging dataset ($^{99m}$Tc-tetrofosmin) may be weighted more strongly than the first functional imaging data type associated with the first functional imaging dataset ($^{123}$I-sodium-iodide).

While the embodiment above described a technique for determining visualization priority based on SUV values, according to other embodiments, the processor 102 may be configured to determine the visualization priority for each of the plurality of voxels based on absolute activity from the region within the patient's volume-of-interest corresponding to each of the plurality of voxels. For example, the visualization priority for each of the plurality of voxels in the patient image space may be determined by comparing the absolute activity level of the first functional imaging data type to the absolute activity level of the second functional imaging data type. As with the previous embodiment, the logical rules stored in the memory 108 may include a weighting factor that is applied to one or more of the functional imaging data types. The processor may be configured to determine the visualization priority for each of the plurality of pixels in the joint-visualization image differently according to various embodiments. For example, other embodiments may not involve determining a visualization priority for each of the plurality of voxels in a patient image volume. According to various other embodiments, the processor 102 may be configured to determine the visualization priority based on a logical comparison of corresponding voxel data from two or more of the functional imaging datasets. Additional details will be described hereinafter.

While the embodiments described above were specific to an embodiment with two functional imaging data types (i.e., a first functional imaging dataset and a second functional imaging dataset), other embodiments may have three or more different functional imaging data types. For example, additional functional imaging datasets may be acquired and accessed by the processor 102. According to an embodiment, a unique radiotracer, including a ligand that is unique from the ligands in the other radiotracers, may be administered to the patient before the acquisition of each additional functional imaging dataset. The additional radiotracer/s may be administered to the patient at generally the same time as the first radiotracer, or according to other embodiments, they may be spaced out by a number of minutes.

Referring back to FIG. 10, at step 797, the processor 102 generates a joint-visualization image after determining the visualization priority for each of the plurality of voxels in the patient image volume. According to many embodiments, the processor 102 may generate the joint-visualization image by generating a rendering based on the patient image volume. FIG. 11 shows a representation of a joint-visualization image 850. The joint-visualization image 850 may be generated based on a rendering using the voxels in the patient image volume according to an embodiment. Next, at step 798, the processor 102 displays the joint-visualization image on the display device, such as the display device 106.

Figure 12:
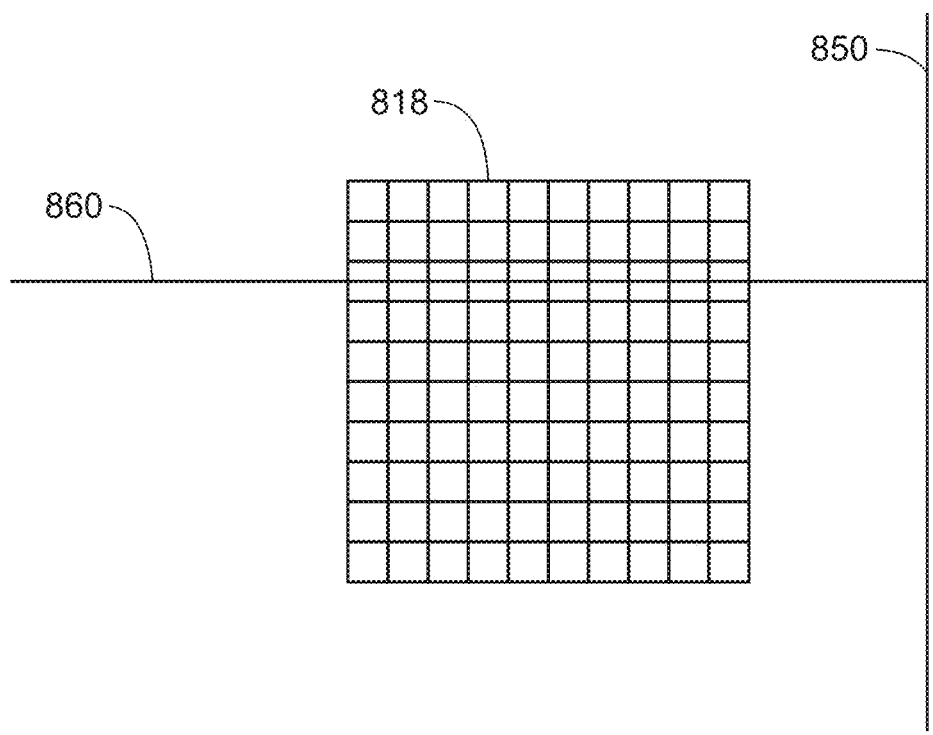
FIG. 12 is a representation of a side view of the patient image volume with respect to a joint-visualization image in accordance with an embodiment.
Figure 13:
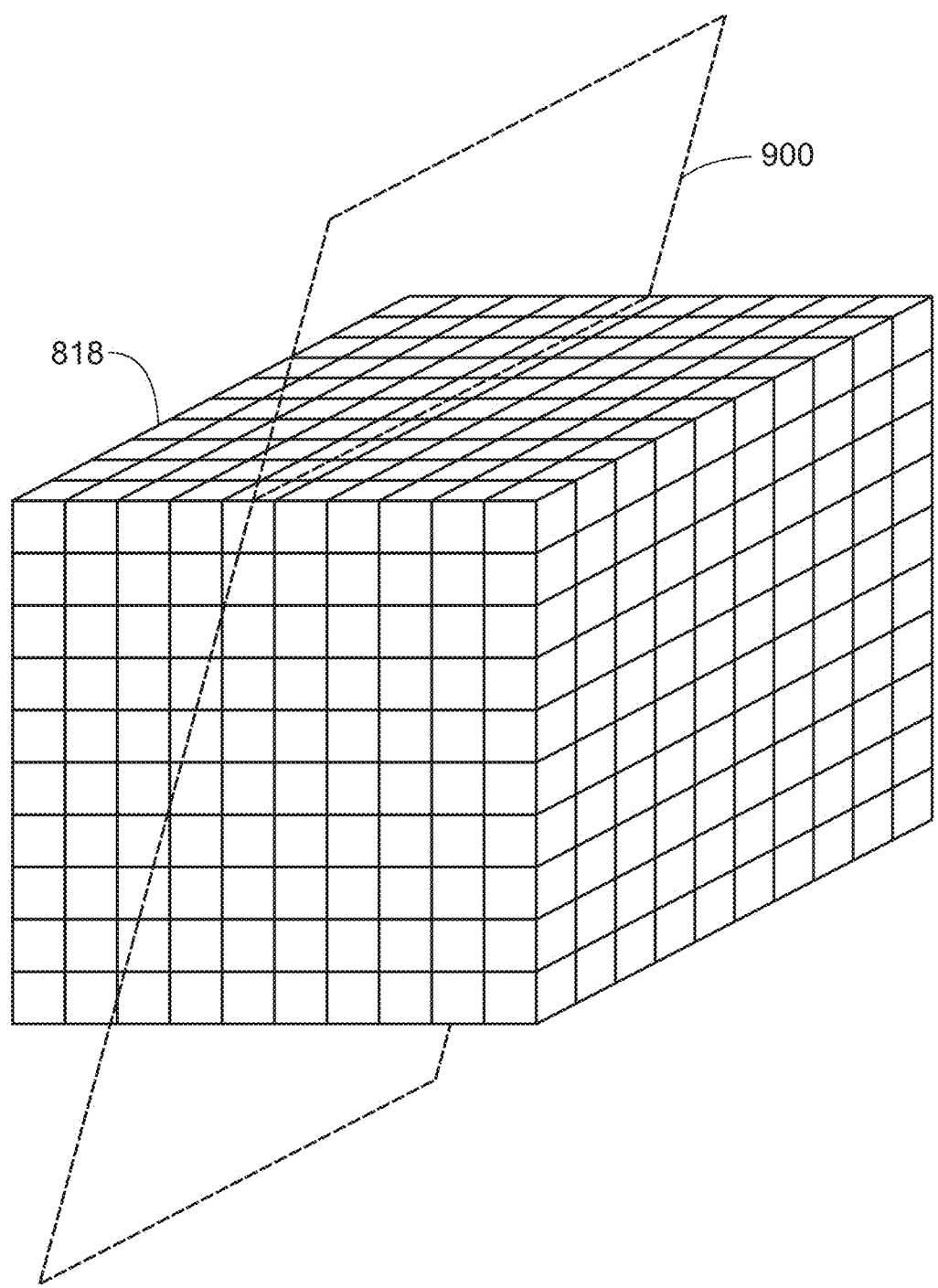
FIG. 13 is a schematic representation of a patient image volume and an image plane in accordance with an embodiment.

FIG. 12 shows a representation of a side-view of the patient image volume 818 with respect to the portion of the joint-visualization image 850. FIG. 13 shows a representation of a perspective view of a single ray through the patient image volume 818 with respect to a portion of the joint-visualization image 851. As shown in FIG. 11, the portion of the joint-visualization image 851 is a sub-region of the joint-visualization image 850. FIG. 12 will be used to explain how the joint-visualization image 850 may be generated in accordance with various embodiments. As described above, after determining the visualization priority, each of the plurality of voxels in the patient image volume 818 represents information from a single one of the plurality of functional imaging datasets. FIG. 12 shows a ray 860 passing through the patient image volume 818. The perspective of the patient image volume 818 is from the side view, so only a single layers of voxels in the patient image volume 818 is visible in FIG. 12. The ray 860 passes intersects a plurality of voxels within the patient image volume 818. The ray 860 shown in FIG. 12 is parallel to some of the surfaces of the voxels, but it should be appreciated that the rays used to generate the joint-visualization image 850 may pass through the patient image volume 818 at any arbitrary angle according to various embodiments. The ultimate value of the pixel in the joint visualization image 850 may be generated based on a ray-casting technique, such as that schematically represented by FIG. 12. According to other embodiments, the values of some of the pixels in the joint-visualization image 850 may be generated by ray-casting, while the values of other pixels may be generated by interpolating between pixel values generated by ray-casting.

The processor 102, may generate a multiplanar reformation image. FIG. 13 shows a schematic representation of the patient image volume 818 and an image plane 900. The multiplanar reformation image is two-dimensional image of an arbitrary plane that is reconstructed from voxel data in the patient image volume. The image plane 900 in FIG. 14 represents an exemplary image plane. The multiplanar reformation image of the image plane 900 is a visual representation of the voxel data intersected by the image plane 900. According to one embodiment, the processor 102 may be configured to apply multiple color-mapping schemes to the voxel data intersected by the image plane 900 after the selection of the image plane. According to other embodiments, the processor 102 may first generate a volume-rendering of the patient image volume 818 and may then generate the multiplanar reformation image based on the volume-rendering. A first of the plurality of pixels in the joint-visualization image 850 may be displayed using a first color-mapping scheme corresponding to the first functional imaging data type (from the first functional imaging dataset); and a second plurality of pixels in the joint-visualization image 850 may be displayed using a second color-mapping scheme corresponding to the second functional imaging data type (from the second functional imaging dataset). This way the clinician may quickly and easily distinguish the pixels associated with the first functional imaging dataset from the pixels associated with the second functional imaging dataset.

According to an exemplary embodiment wherein both the first and second functional imaging datasets are registered to a first anatomical imaging dataset and a second anatomical imaging dataset, respectively, registering the first functional imaging dataset to the second functional imaging dataset may be performed by registering the first anatomical imaging dataset to the second anatomical imaging dataset.

While the joint-visualization image may be displayed alone, in many applications, the joint-visualization image will be displayed as an overlay on an anatomical image in a fusion mode. Referring to the method 750 shown in FIG. 8, the anatomical image may be generated from the first CT dataset, which was a full-dose CT dataset. According to other embodiments, the anatomical image may be generated from the second CT dataset. The anatomical image generated from the CT dataset includes anatomical details of a much higher resolution than those shown in the joint-visualization image, based on portions of the first and second PET datasets. As discussed previously, the functional imaging datasets (i.e. the PET datasets) may be registered to anatomical imaging dataset (i.e., the CT dataset) when the data is acquired with a hybrid PET-CT imaging system. It is therefore relatively easy to register the joint-visualization image (generated from the PET datasets) to the anatomical image (generated from the first CT dataset).

Figure 14A:
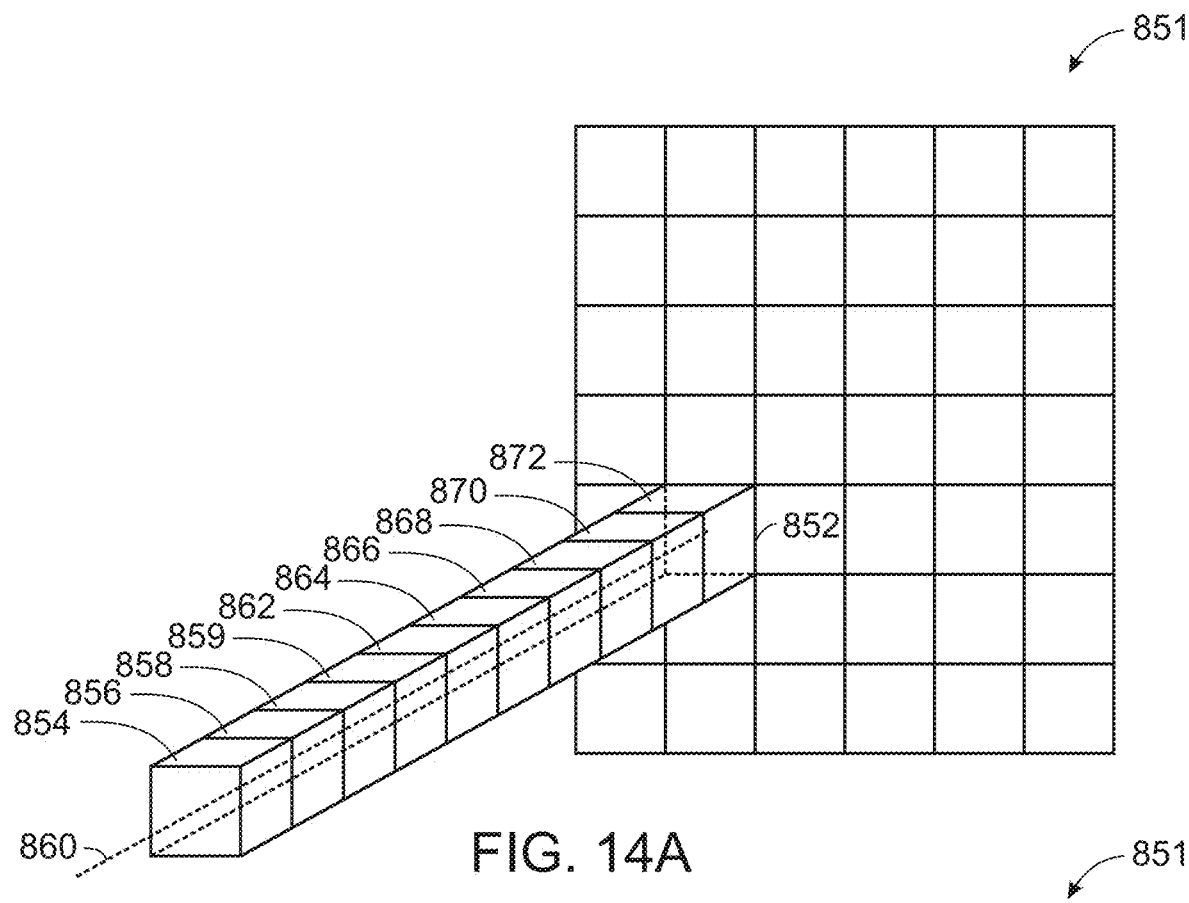
FIG. 14A is a representation of a perspective view of a single ray through a patient image volume with respect to the joint-visualization image in accordance with an embodiment.
Figure 14B:
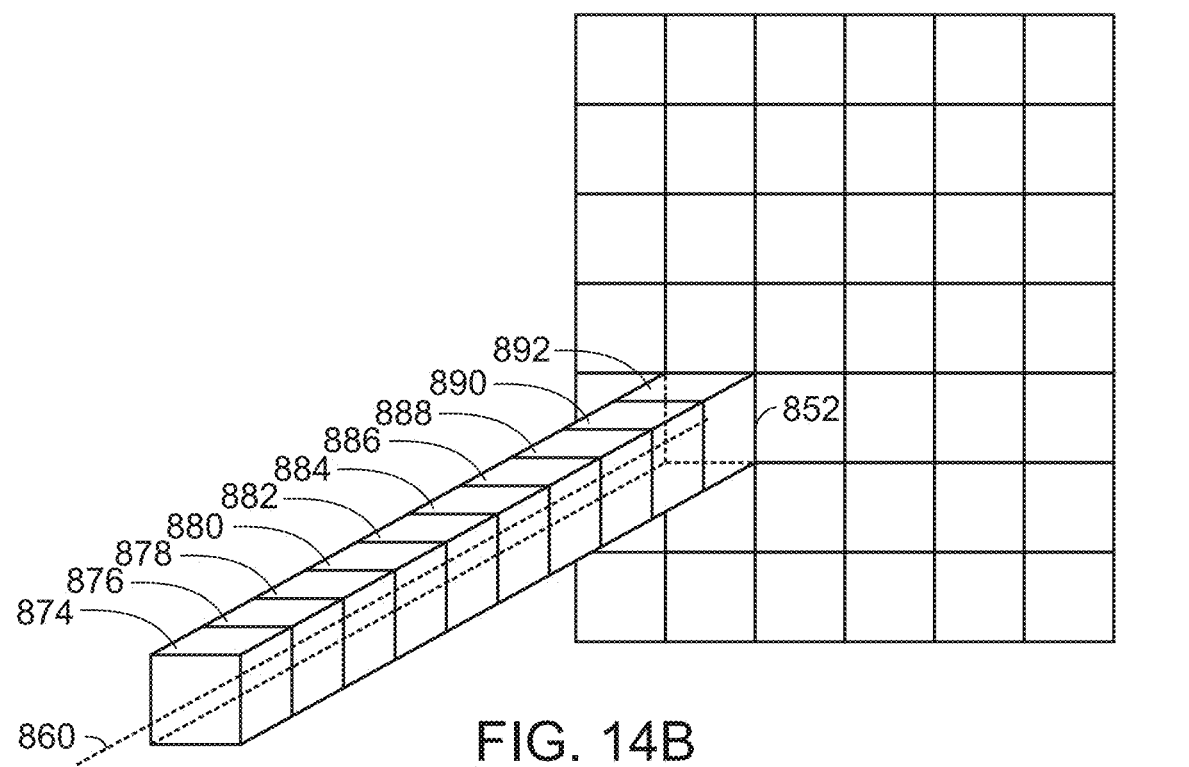
FIG. 14B is a representation of a perspective view of a single ray through a patient image volume with respect to the joint-visualization image in accordance with an embodiment.

As mentioned previously, determining the visualization priority for each of the plurality of pixels in the joint-visualization image may not involve determining a visualization priority for each of the plurality of voxels according to various embodiments. For example, the processor 102 may be configured to determine the visualization priority based on a logical comparison of corresponding voxel data from two or more of the functional imaging datasets. This may be used, for instance, when the joint-visualization image is a MIP image or a MinIP image. FIG. 14A and FIG. 14B will be used to explain an exemplary embodiment.

FIG. 14A shows a schematic representation of the ray 860 passing through a plurality of voxels associated with a first functional imaging dataset and FIG. 14B shows a schematic representation of the ray 860 passing through a plurality of voxels associated with a second functional imaging dataset. Only 10 voxels are schematically represented in FIG. 14A, but it should be appreciated that ray-casting would typically involve casting a ray through a significantly larger number of voxels according to most embodiments. FIG. 14A includes a first voxel 854, a second voxel 856, a third voxel 858, a fourth voxel 859, a fifth voxel 862, a sixth voxel 864, a seventh voxel 866, an eighth voxel 868, a ninth voxel 870, and a tenth voxel 872. As discussed previously, each of the voxels (854, 856, 858, 859, 862, 864, 866, 868, 870, and 872) represents information from only one of the plurality of functional imaging data types. According to an embodiment, each of the voxels (854, 856, 858, 859, 862, 864, 866, 868, 870, and 872) represents the first functional imaging data type (from the first functional imaging dataset).

According to an embodiment where the joint-visualization image is a maximum-intensity-projection (MIP) image, each pixel on the joint-visualization image 850 represents that maximum pixel value along the ray. So, the pixel 852 would represent the value of the maximum voxel along the ray 860. Assuming that the seventh voxel 866 has the highest value of the voxels (854, 856, 858, 859, 862, 864, 866, 868, 870, and 872), then the pixel 852 would represent the information in voxel 866.

Similarly, for a minimum-intensity-projection (MinIP) image, the processor 102 may identify the voxel along each ray, such as the ray 860, with the minimum value. The processor 102 would then assign the value and functional imaging data type of the voxel with the minimum value to the associated pixel, such as the pixel 852. Assuming that the first voxel 854 had the minimum value of all the voxels along the ray 860, the pixel 852 would be assigned the value of the first voxel.

For embodiments where the joint-visualization image is either a MIP image or a MinIP image, a MIP or MinIP value from each of the functional imaging datasets is associated with each of the pixels. For this reason, it is necessary to determine a visualization priority for each of the plurality of pixels to define which one of the plurality of functional imaging data types is represented by each pixel in the joint-visualization image. As discussed previously, the processor 102 may determine a visualization priority for each pixel in the joint-visualization image by performing a logical comparison of corresponding information in each of the plurality of functional imaging datasets. For embodiments where the joint-visualization image is a maximum-intensity-projection (MIP) image, the processor 102 may compare a first maximum-intensity projection (MIP) value calculated from a first functional imaging dataset with a second maximum-intensity-projection (MIP) value calculated from a second functional imaging dataset. For embodiments where the joint-visualization image is a minimum-intensity-projection (MinIP) image, the processor 102 may compare a first minimum-intensity projection (MinIP) value calculated from a first of the plurality of datasets with a second minimum-intensity-projection (MinIP) value calculated from a second of the plurality of functional imaging datasets.

As discussed previously, FIG. 14A shows a representation of a perspective view of a single ray through a patient image volume with respect to a portion of the joint-visualization image 851. For embodiments where the joint-visualization image 851 is a MIP image, the processor 102 may calculate a first maximum-intensity-projection (MIP) value from the first functional imaging dataset and compare it to a second maximum-intensity-projection (MIP) values from the second functional imaging dataset. As discussed above, the processor 102 may be configured to determine the visualization priority for each pixel in the joint-visualization image based on a logical comparison of corresponding information in each of the plurality of functional imaging datasets. According to an embodiment, the first functional imaging dataset may represent a first functional imaging data type and a second functional imaging dataset may represent a second functional imaging data type. In order to determine the visualization priority for pixel 852, the processor 102 may first identify a first maximum-intensity-projection value from the first functional imaging dataset and a second maximum-intensity-projection value from the second functional imaging dataset. The processor 102 may then perform a logical comparison of the first maximum-intensity-projection value from the first functional imaging dataset with the second maximum-intensity-projection value from the second functional imaging dataset using one or more logical rules. FIG. 14A shows ray 860 with respect to voxels from the first functional imaging dataset. The corresponding information from the second functional imaging dataset is from a corresponding sub-volume within the volume-of-interest. FIG. 14B show ray 860 with respect to voxels from the second functional imaging dataset. Voxels 874, 876, 878, 880, 882, 884, 886, 888, 890, and 892 represents information acquired from the same sub-volumes of the patient as voxels 854, 856, 858, 859, 862, 864, 866, 868, 870, and 872 (shown in FIG. 14A) The voxels used to calculate the first MIP value correspond to the same sub-volume in the patient as the voxels used to calculate the second MIP value. For example, voxels 854, 856, 858, 859, 862, 864, 866, 868, 870, and 872 may represent information from the first functional imaging dataset and the MIP value may therefore represent the first MIP value. A second MIP value would be calculated from voxels 874, 876, 878, 880, 882, 884, 886, 888, 890, and 892 in the second functional imaging dataset. FIG. 14A represents how a first MIP value (from the first functional imaging dataset) may be calculated for pixel 852 and FIG. 14B represents how a second MIP value (from the second functional imaging dataset) may be calculated for pixel 852.

The processor 102 may then perform a logical comparison of the first MIP value and the second MIP value in order to determine a visualization priority for pixel 852. The processor 102 may determine the visualization priority for each pixel based on the SUV values of the first and second functional imaging datasets. For example, each of the voxel values may represent an SUV value. The processor 102 may be configured to determine the visualization priority by applying logical rules stored in the memory 108. As discussed earlier, the logical rules may establish rules or thresholds to determine which one of the functional imaging data types should be represented by each of the plurality of pixels. According to an embodiment, the processor 102 may assign visualization priority to the functional imaging data type with the highest SUV value. For example, each pixel in the joint-visualization image may represent information from the functional imaging dataset with the highest SUV value. For example, with respect to the pixel 852, if the MIP value associated with the first functional imaging data type is higher than MIP value associated with the second functional imaging data type then that particular voxel would be assigned a visualization priority of the first functional imaging data type (associated with the first functional imaging dataset). On the other hand, for pixel 852, if MIP value associated with the second functional imaging data type is higher than MIP value associated with the first functional imaging data type, then the processor 102 would assign a visualization priority of the second functional imaging data type (associated with the second functional imaging dataset) to pixel 852. The processor 102 may proceed to individually assign visualization priorities to each of the pixels in the joint-visualization image according to the method described hereinabove.

According to another embodiment, the processor 102 may be configured to apply a weighting factor to one or more of the functional imaging data types in order to emphasis one or more of the plurality of data types. For example, the logical rules stored in the memory 108 may include a weighting factor that is applied to one or more of the functional imaging data types. For example, the logical rules may emphasize one of the functional imaging data types by one or both of applying a weighting factor of greater than 1 (such as 1.25, 1.5, 1.75, etc.) to the SUV values from one of the functional imaging datasets to emphasize that functional imaging data type associated with the one of the functional imaging datasets; or applying a weighting factor of less than 1 (such as 0.25, 0.5, 0.75, etc.) to another of the functional imaging data types associated with a different one of the functional imaging datasets. For example, to emphasize the first functional imaging data type, associated with the first functional imaging dataset ($^{123}$I-sodium-iodide), the weighting factor may include one or both of applying a weighting factor of greater than 1 to the SUV values generated from the first functional imaging dataset or applying a weighting factor of less than 1 to the SUV values generated form the second functional imaging dataset. According to other embodiments, various weighting factors may be applied to a MIP value or a MinIP value calculated from the each of the functional imaging datasets in order to more-strongly emphasis one of the functional imaging data types. After applying the one or more weighting factors, weighted SUV data, including weighted SUV values, is created. According to an exemplary embodiment, the processor 102 may assign visualization priority to each of the plurality of pixels by selecting the functional imaging data type associated with the functional imaging dataset with the highest weighted SUV value. The embodiment described above would weight the first functional imaging data type associated with the first functional imaging dataset more strongly than the second functional imaging data type associated with the second functional imaging dataset. According to other embodiments, the logical rules may be configured to weight one or more different functional imaging data types. For example, the second functional imaging data type, associated with the second functional imaging dataset may be weighted more strongly than the first functional imaging data type associated with the first functional imaging dataset.

While the embodiment above described a technique for determining visualization priority based on SUV values, according to other embodiments, the processor 102 may be configured to determine the visualization priority for each of the plurality of pixels based on absolute activity from the region within the patient's volume-of-interest corresponding to each of the plurality of pixels. For example, the visualization priority for each of the plurality of pixels in the joint-visualization image may be determined by comparing the absolute activity level of the first functional imaging data type to the absolute activity level of the second functional imaging data type. As with the previous embodiment, the logical rules stored in the memory 108 may include a weighting factor that is applied to one or more of the functional imaging data types. For embodiments where the joint-visualization image is a MinIP image, the processor 102 may be configured to determine the visualization priority for each of the pixels by comparing a first minimum-intensity-projection (MinIP) value calculated from along a ray through a first functional imaging dataset with a second minimum-intensity-projection (MinIP) value calculated along a ray with a corresponding position through the second functional imaging dataset. The processor 102 may, for each pixel in the joint-visualization image, select the functional imaging data type from the functional imaging dataset with the lower MinIP value. According to other embodiments, the processor 102 may be configured to determine the visualization priority for each pixel in the joint-visualization image based on any number of logical rules comparing corresponding voxel values between two or more different functional imaging datasets.

While the embodiments described above were specific to an embodiment with two functional imaging data types, other embodiments may have three or more different functional imaging data types. For example, additional functional imaging datasets may be acquired and accessed by the processor 102. According to an embodiment, a unique radiotracer, including a ligand that is unique from the ligands in the other radiotracers, may be administered to the patient before the acquisition of each additional functional imaging dataset. The additional radiotracer/s may be administered to the patient at generally the same time as the first radiotracer, or according to other embodiments, they may be spaced out by a number of minutes.

Each pixel in the joint-visualization image 850 represents only a single one of the plurality of functional imaging data types. For example, in the embodiment discussed with respect to FIG. 8, each pixel represents either the first functional imaging data type (from the first functional imaging dataset acquired using $^{68}$Ga-FAPI) or the second functional imaging data type (from the second functional imaging dataset acquired using $^{18}$F-FDG). For the pixels in the joint-visualization image, a first color-mapping scheme may be used to represent pixels associated with a first of the plurality of functional imaging datasets and a second, different, color-mapping scheme may be used to represent pixels associated with a second of the plurality of functional imaging datasets. Regarding the embodiment described with respect to FIG. 8, a first of the plurality of pixels in the joint-visualization image 850 may be displayed using a first color-mapping scheme corresponding to the first functional imaging data type (from the first functional imaging dataset acquired using $^{68}$Ga-FAPI) and a second plurality of pixels in the joint-visualization image 850 may be displayed using a second color-mapping scheme corresponding to the second functional imaging data type (from the second functional imaging dataset acquired using $^{18}$F-FDG). The visualization priority for each of the plurality of pixels in the joint-visualization image may be determined according to the methods described hereinabove with respect to MIP and MinIP images in any of the previously described embodiments. For example, one or more of these techniques may be used at step 306 of the method 300, at step 768 of the method 750, or at step 796 of the method 780. Additionally, one or more of these techniques may be used at step 988 of the method 980 (shown in FIG. 16), which has not been described in detail yet.

The processor 102 may, for example, access one or more look-up tables stored in the memory 108 in order to determine how to represent each pixel. There may, for instance, be a separate color-mapping scheme stored in each look-up table. According to an exemplary embodiment, the processor 102 may access a first look-up table for a first color-mapping scheme in order to generate the colors and values for the first plurality of pixels associated with the first functional imaging data type and the processor 102 may access a second look-up table for a second color-mapping scheme in order to generate the colors and values for the second plurality of pixels associated with the second functional imaging data type. The first color-mapping scheme is different than the second color-mapping scheme. According to other embodiments, the first color-scheme may include a range of colors. For example, the first color-mapping scheme may include colors that fall within the hues of red, orange, and yellow; and the second color-mapping scheme may include colors that fall within the hues of green, blue, and purple. It should be appreciated that each color-mapping scheme may include a different range of colors according to various embodiments. According to an embodiment, the first color-mapping scheme may be primarily a first color and the second color-mapping scheme may be primarily a second color that is different than the first color. According to an embodiment, the first color may be red, and the second color may be blue, but each color-mapping schemes may include any one or more colors according to various embodiments. Each color-mapping scheme used to generate the joint-visualization image may map the same value to a different color. For example, the first color-mapping scheme may map a first value to a first color while a second color-mapping scheme may map the same first value to a second color that his different than the first color. According to an embodiment, on the joint-visualization image, all the pixels representing the first functional imaging data type (from the first functional imaging dataset) may be represented primarily in the first color and all the pixels representing the second functional imaging data type (from the second functional imaging dataset) may be represented primarily in the second color. This way, the clinician will be able to quickly and easily tell, for each pixel, if the data on the joint-functional image is from the first functional imaging dataset or the second functional imaging dataset based on the color-scheme used to display each respective pixel.

Figure 15:
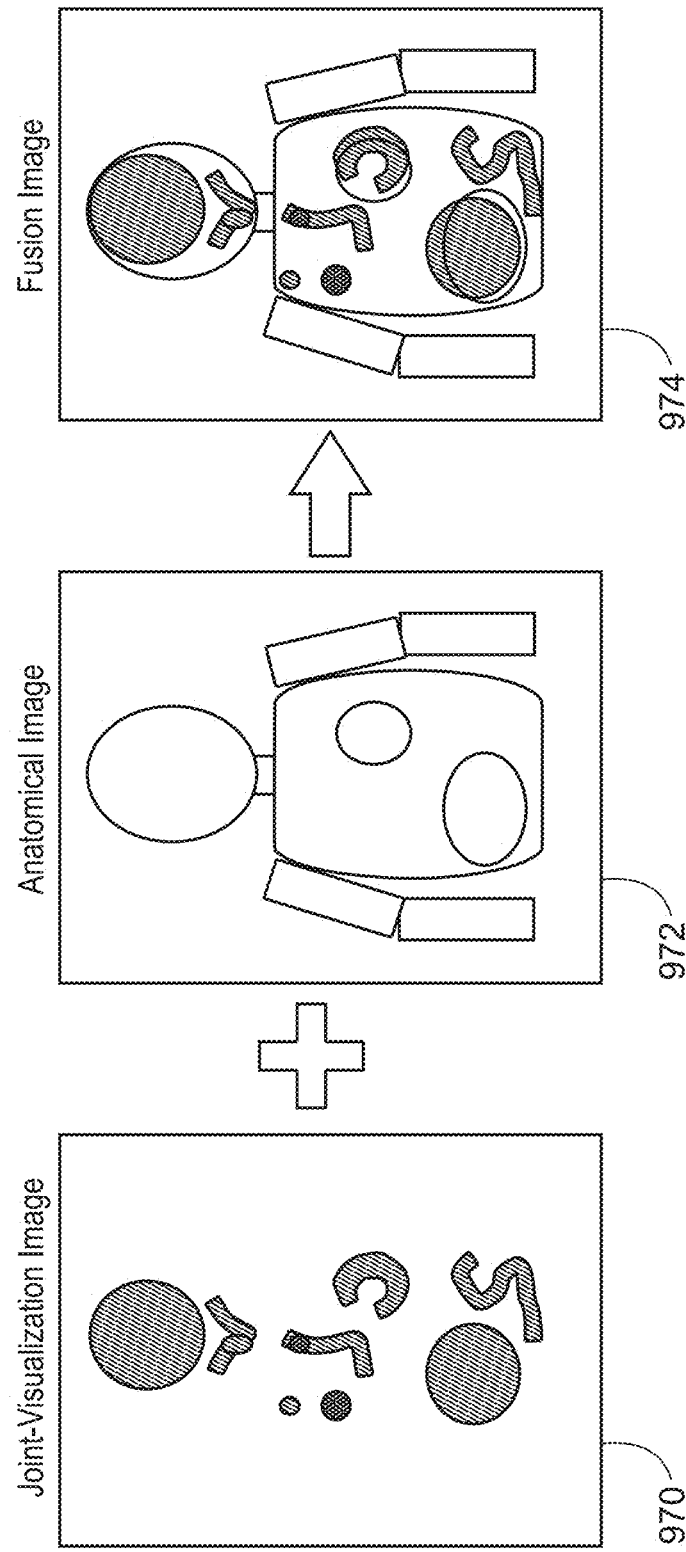
FIG. 15 is a schematic illustration of a fusion image in accordance with an exemplary embodiment.

FIG. 15 is a schematic illustration of fusion image in accordance with an exemplary embodiment. FIG. 15 includes a joint-visualization image 970, an anatomical image 972, and a fusion image 974. The joint-visualization image 970 may include information from any two or more different functional imaging data types. The joint-visualization image may include information acquired with two or more different PET radiotracers, information acquired using two or more different SPECT radiotracers, information acquired using one or more PET radiotracers and one or more SPECT radiotracers, or information acquired with an fMRI imaging system and information acquired with one or more PET tracers and/or information acquired with one or more SPET tracers.

The anatomical image may be generated from an anatomical imaging dataset such as an CT anatomical imaging dataset, an MRI anatomical imaging dataset or an ultrasound anatomical imaging dataset. For embodiments using a hybrid imaging system, such as a PET-CT imaging system, a SPECT-CT imaging system, an MRI-PET imaging system or an MRI-SPECT imaging system, it is anticipated that the anatomical imaging dataset will be either a CT anatomical imaging dataset or an MRI anatomical imaging dataset, respectively.

The fusion image 974 is generated by overlaying the joint-visualization image 970 on the anatomical image 972. According to an embodiment, the anatomical image may be represented in greyscale and the joint-visualization image may be represented using one or more different colors. According to various embodiments one or both of the joint-visualization image 970 and the anatomical image 972 may be displayed in a semi-transparent manner in the fusion image 974 so that the user may see information from both anatomical image and the joint-visualization image in the fusion image 974. According to various embodiments, the clinician may adjust the transparency levels of one or both of the joint-visualization image 970 and the anatomical image 972 in the fusion image 974 in order to adjust the relative impact of the two images (i.e., the joint-visualization image and the anatomical image) in the fusion image 974. According to some embodiment the clinician may adjust the transparency levels of the joint-visualization image 970 and the anatomical image 972 in the fusion image 974 via the user interface by adjusting one or two slide bars or one or two virtual slide bars.

Figure 16:
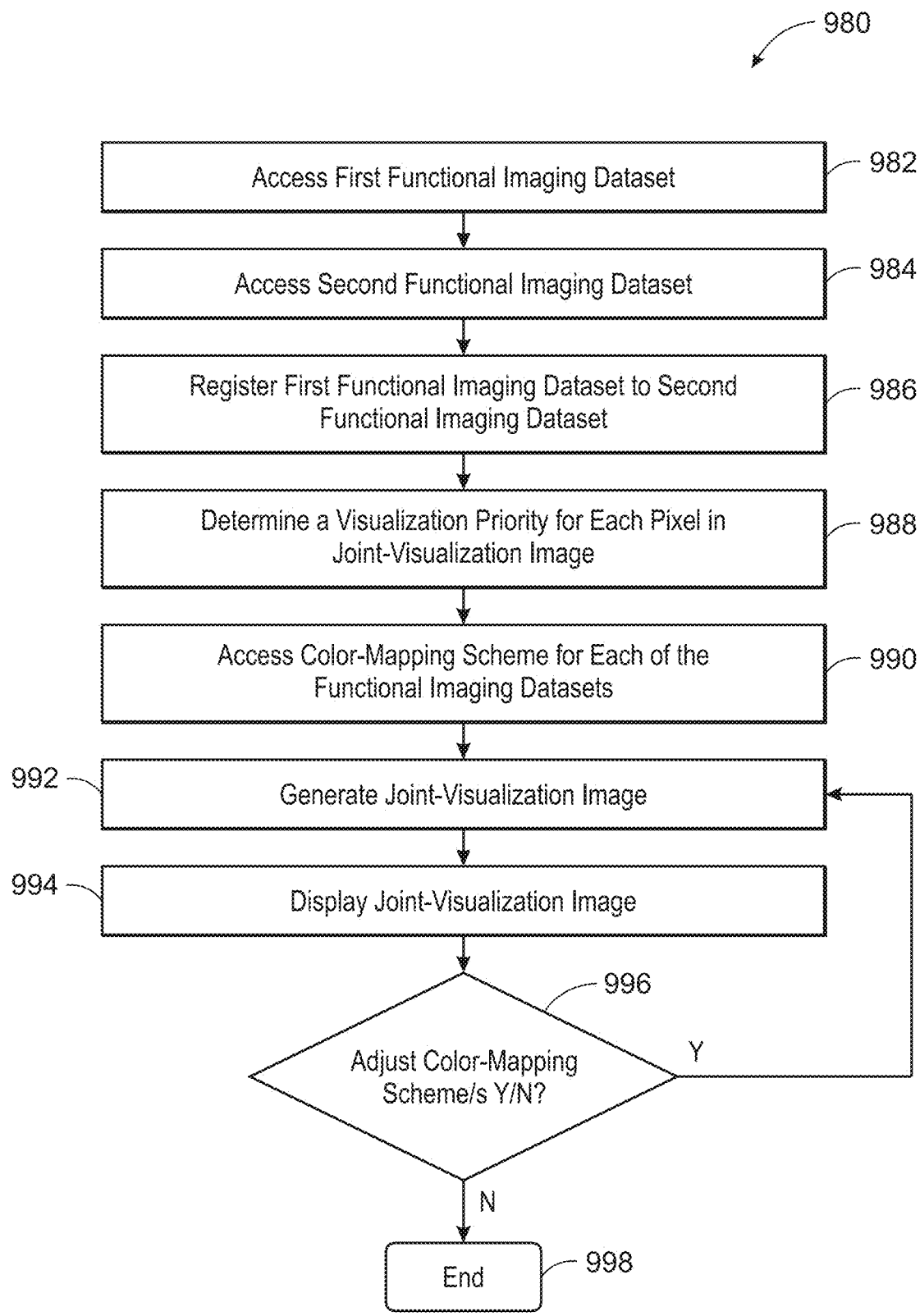
FIG. 16 is a flow chart of a method in accordance with an embodiment.

According to various embodiments, the clinician may be able to adjust one or more of the color-mapping schemes used to generate the joint-visualization image. FIG. 16 is a flow chart of a method 980 which will be used to describe an exemplary embodiment where one or more color mapping schemes are adjusted. The method 980 shown in FIG. 16 may be performed with a workstation, such as the workstations 100 shown in FIG. 1. The technical effect of the method 980 is the display of joint-visualization image on the display device 106. The joint-visualization image 970 represents information from a plurality of functional imaging data types at the same time.

At step 982, the processor 102 accesses a first functional imaging dataset. At step 984, the processor 102 accesses a second functional imaging dataset. At step 986, the processor registers the first functional imaging dataset to the second functional imaging dataset. At step 988, the processor 102 determines a visualization priority for each pixel in a joint-visualization image based on a logical comparison of corresponding information in each of the plurality of functional imaging datasets. The processor 102 may determine the visualization priority using, for example, any of the previously-discussed techniques. Next, at step 990, the processor 102 accesses a color-mapping scheme for each of the functional imaging datasets. Since the embodiment 980 includes a first functional imaging dataset and a second functional imaging dataset, the processor 102 may access a first color-mapping scheme to represent the first of the functional imaging datasets and a second color-mapping scheme to represent the second of the functional imaging datasets. The first color-mapping scheme is different than the second color-mapping scheme. At step 992, the processor 102 generates a joint-visualization image and at step 994, the processor displays the joint-visualization imaging on a display device. Steps 982, 984, 986, 988, 990, 992, and 994 correspond with steps that were previously described with respect to the method 300, shown in FIG. 3, and the method 750, shown in FIG. 8, and, as such, will not be described in additional detail.

At step 996 of the method 980, the processor 102 may receive in input from the user interface 104 adjusting a color-mapping scheme. If an input is not received at step 996, the method 980 may advance to step 998 where it ends. However, if an input is received from the user interface, the method 980 returns to step 992, and steps 992 and 994 are performed again. The input received at step 996 from the user interface 104 may adjust one or more of the color-mapping schemes used to generate the joint-visualization image. The processor 102 may receive an adjustment to the first color-mapping scheme and/or the second color-mapping scheme according to various embodiments. At step 992, the processor 102 generates an updated joint-visualization image using the adjusted color-mapping scheme/s. The updated joint-visualization image may be displayed on the display device in place of the previously displayed joint visualization image. The method 980 may iteratively repeat steps 992, 994, and 996 as many times as it is desired to adjust one or more of the color-mapping schemes. This allows the clinician to adjust the colors used in each color-mapping scheme in order to help visualize one or more regions on the joint-visualization image more clearly. As described with respect to previous embodiments, the joint-visualization image may be displayed as an overlay on an anatomical image in a fusion mode according to various embodiments.

The functional imaging data may be rescaled for any of the embodiments described herein. For example, a useful baseline reference can be the calculated typical activity of normal tissues in the specific scanned patient. This can be calculated by, for example, first segmenting the overall soft-tissues using the anatomical CT image data (from the PET-CT protocol) and then calculating the median activity of these voxels (on the PET image data). Based on this process, a visualization priority threshold can be set, for example, as image values larger than the baseline value or larger than twice of the baseline value, etc. The principle of re-scaling the image data relative to the normal tissue value, can be applied for MRI or any other functional imaging modality according to various embodiments.

There are numerous advantages provided by various embodiments of the invention. For example, embodiments provide a method for displaying a joint-visualization image representing information from multiple different functional imaging data types. For example, the multiple different functional imaging data types may have been acquired using two or more different radiotracers. Embodiments of the invention involve displaying information from each of the different functional imaging datasets with a unique quantitative scale. For example, information from a first functional imaging dataset may be displayed with a first quantitative scale while information from a second functional imaging dataset may be displayed with a second, different, quantitative scale. The quantitative scale used to represent the information in each particular functional imaging dataset may be unique to that particular functional imaging dataset. Since it is not necessary to display values from multiple functional imaging datasets on the same quantitative scale, it is possible to optimize each quantitative scale based on the data within that particular functional imaging dataset. This allows the quantitative scale used for each functional imaging dataset be a better fit to the range of data values within that particular functional imaging dataset. This, in turn, enables the processor 102 to more-accurately display the relevant differences within a particular functional imaging dataset. For example, if all of the value for a particular functional imaging dataset are compressed within a small range of values, it may be desirable to use a different quantitative scale than for a dataset with data values that extend over a much larger range of values. According to various embodiments, one or more of the quantitative scales may be adjusted either manually or based on a particular clinical application. Additionally, as discussed previously, embodiments may further involve displaying the joint-visualization image as an overlay on an anatomical image in a fusion mode. This provides clinician with information from two or more different functional imaging data types at the same time as an anatomical image in order to provide the clinician with additional anatomical context when viewing and interpreting the image. Various embodiments provide the clinician with an easy and intuitive way to view and interact with multiple different types of data (i.e., multiple different anatomical imaging data types and anatomical imaging data). This can help save time and results in a faster and easier way to make a diagnosis for certain clinical situations. Additionally, various embodiments of the invention involve determining a visualization priority for each of a plurality of pixels in the joint-visualization image. This means that each pixel represents information from only a single one of the functional imaging data types. This is an improvement over conventional solutions which sometimes try to represent multiple different types of functional imaging data in a single pixel. With these conventional solutions, it is difficult or impossible to determine if the pixel value in the displayed image is based on a first type of functional imaging data or a second type of functional imaging data. The invention makes a significant improvement because each pixel in the joint-visualization image represents only a single functional imaging data type, which makes the interpretation of the joint-visualization image easier.

The techniques presented and claimed herein are referenced and applied to material objects and concrete examples of a practical nature that demonstrably improve the present technical field and, as such, are not abstract, intangible or purely theoretical.

This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of functional imaging comprising:
   accessing a plurality of functional imaging datasets acquired from a volume-of-interest, wherein each of the plurality of functional imaging datasets is a different one of a plurality of functional imaging data types;
   registering the plurality of functional imaging datasets to each other;
   determining a visualization priority for each of a plurality of pixels in a joint-visualization image based on a logical comparison of corresponding information in each of the plurality of functional imaging dataset, wherein the visualization priority defines which one of the plurality of functional imaging data types will be represented by each of the plurality of pixels, wherein the joint-visualization image includes one of a maximum-intensity-projection (MIP) image or a minimum-intensity-projection (MinIP) image, and wherein said performing the logical comparison of corresponding information includes either: comparing a first maximum-intensity-projection (MIP) value calculated from a first of the plurality of functional imaging datasets with a second maximum-intensity-projection (MIP) value calculated from a second of the plurality of functional imaging datasets when the joint-visualization image is a maximum-intensity projection (MIP) image; or comparing a first minimum-intensity-projection (MinIP) value calculated from the first of the plurality of functional imaging datasets with a second minimum-intensity-projection (MinIP) value calculated from the second of the plurality of functional imaging datasets when the joint-visualization image is a minimum-intensity-projection (MinIP) image;
   generating the joint-visualization image based on the visualization priority determined for each of the plurality of pixels and at least a portion of each of the plurality of functional imaging datasets, wherein the joint-visualization image represents information from each of the plurality of functional imaging data types at the same time, and wherein each of the plurality of pixels in the joint-visualization image represents only a single one of the plurality of functional imaging data types; and
   displaying the joint-visualization image on a display device.

2. The method of claim 1, wherein the joint-visualization image is selected from the list consisting of a maximum-intensity-projection (MIP) image, a minimum-intensity-projection (MinIP) image, and a multiplanar reformation image.

3. The method of claim 1, wherein determining the visualization priority for each of the plurality of pixels is based on a highest standard uptake value of each of the plurality of functional imaging data types.

4. The method of claim 1, wherein said generating the joint-visualization image comprises using a first color-mapping scheme to represent a first of the plurality of functional imaging datasets and using a second color-mapping scheme that is different than the first color-mapping scheme to represent a second of the plurality of functional imaging datasets.

5. The method of claim 4, further comprising:
   adjusting the first color-mapping scheme;
   generating an updated joint-visualization image using the adjusted first color-mapping scheme and the second color-mapping scheme;
   displaying an updated joint-visualization image on the display device.

6. The method of claim 4, further comprising:
   adjusting both the first color-mapping scheme and the second color-mapping scheme;
   generating an updated joint-visualization image on the display device using the adjusted first color-mapping scheme and the adjusted second color-mapping scheme; and
   displaying the updated joint-visualization image on the display device.

7. The method of claim 1, wherein a first of the plurality of functional imaging datasets was acquired using a first radiotracer and a second of the plurality of functional imaging datasets was acquired using a second radiotracer, wherein the second radiotracer includes a different ligand than the first radiotracer.

8. The method of claim 1, wherein a first of the plurality of functional imaging datasets was acquired using a first functional imaging modality and a second of the plurality of functional imaging datasets was acquired using a second functional imaging modality, wherein the second functional imaging modality is different than the first functional imaging modality.

9. The method of claim 1, further comprising:
   accessing an anatomical imaging dataset;
   wherein said registering the plurality of functional imaging datasets to each other comprises registering each of the plurality of functional imaging datasets to the anatomical imaging dataset; and
   generating an anatomical image from the anatomical imaging dataset;

wherein said displaying the joint-visualization image comprises displaying the joint-visualization image as an overlay on the anatomical image in a fusion mode.

10. A workstation comprising:
a display device; and
a processor coupled to a memory, wherein the processor is configured to apply rules stored in the memory to:
access a plurality of functional imaging datasets acquired from a volume-of-interest, wherein each of the plurality of functional imaging datasets is a different one of a plurality of functional imaging data types;
register the plurality of functional imaging datasets to each other;
determine a visualization priority for each of a plurality of pixels in a joint-visualization image based on a logical comparison of corresponding information in each of the plurality of functional imaging datasets, wherein the visualization priority defines which one of the plurality of functional imaging data types will be represented by each of the plurality of pixels, wherein the joint-visualization image comprises one of a maximum-intensity-projection (MIP) image or a minimum-intensity-projection (MinIP) image, and wherein the processor is configured to perform the logical comparison by either: comparing a first maximum-intensity-projection (MIP) value calculated from a first of the plurality of functional imaging datasets with a second maximum-intensity-projection (MIP) value calculated from a second of the plurality of functional imaging datasets when the joint-visualization image is a maximum-intensity projection (MIP) image; or comparing a first minimum-intensity-projection (MinIP) value calculated from the first of the plurality of functional imaging datasets with a second minimum-intensity-projection (MinIP) value calculated from the second of the plurality of functional imaging datasets when the joint-visualization image is a minimum-intensity-projection (MinIP) image;
generate the joint-visualization image based on the visualization priority determined for each of the plurality of pixels and at least a portion of each of the plurality of functional imaging datasets, wherein the joint-visualization image represents information from each of the plurality of functional imaging data types at the same time, and wherein each of the plurality of pixels in the joint-visualization image represents only a single one of the plurality of functional imaging data types; and
display the joint-visualization image on the display device.

11. The workstation of claim 10, wherein the joint-visualization image is selected from the list consisting of a maximum-intensity-projection (MIP) image, a minimum-intensity-projection (MinIP) image, and a multiplanar reformation image.

12. The workstation of claim 10, wherein the processor is configured to individually determine the visualization priority for each of the plurality of pixels based on a highest standard uptake value of each of the plurality of functional imaging data types.

13. The workstation of claim 10, wherein the processor is configured to generate the joint-visualization image using a first color-mapping scheme to represent a first of the plurality of functional imaging datasets and using a second color-mapping scheme that is different than the first color-mapping scheme to represent a second of the plurality of functional imaging datasets.

14. The workstation of claim 13, wherein the processor is further configured to:
adjust the first color-mapping scheme;
generate an updated joint-visualization image using the adjusted first color-mapping scheme and the second color-mapping scheme;
display an updated joint-visualization image on the display device.

15. The workstation of claim 13, wherein the processor is further configured to:
adjust both the first color-mapping scheme and the second color-mapping scheme;
generate an updated joint-visualization image on the display device using the adjusted first color-mapping scheme and the adjusted second color-mapping scheme; and
display the updated joint-visualization image on the display device.

16. The workstation of claim 10, wherein a first of the plurality of functional imaging datasets was acquired using a first radiotracer and a second of the plurality of functional imaging datasets was acquired using a second radiotracer, wherein the second radiotracer includes a different ligand than the first radiotracer.

17. The workstation of claim 10, wherein a first of the plurality of functional imaging datasets was acquired using a first functional imaging modality and a second of the plurality of functional imaging datasets was acquired using a second functional imaging modality, wherein the second functional imaging modality is different than the first functional imaging modality.

18. The workstation of claim 10, wherein the processor is further configured to:
access an anatomical imaging dataset;
wherein said registering the plurality of functional imaging datasets to each other comprises registering each of the plurality of functional imaging datasets to the anatomical imaging dataset; and
generate an anatomical image from the anatomical imaging dataset;
wherein said displaying the joint-visualization image comprises displaying the joint-visualization image as an overlay on the anatomical image in a fusion mode.

* * * * *